(12) United States Patent
Anker et al.

(10) Patent No.: US 7,417,038 B1
(45) Date of Patent: Aug. 26, 2008

(54) METHODS OF TREATING CACHEXIA

(75) Inventors: Stefan Dietmar Anker, London (GB); Andrew Justin Stewart Coats, London (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 09/807,558

(22) PCT Filed: Oct. 15, 1999

(86) PCT No.: PCT/GB99/03302

§ 371 (c)(1), (2), (4) Date: Jul. 17, 2001

(87) PCT Pub. No.: WO00/21509

PCT Pub. Date: Apr. 20, 2000

(30) Foreign Application Priority Data

| Oct. 15, 1998 | (GB) | 9822458.7 |
| Oct. 15, 1998 | (GB) | 9822459.5 |
| Jul. 23, 1999 | (GB) | 9917181.1 |

(51) Int. Cl.
*A61K 31/58* (2006.01)
*A61K 31/585* (2006.01)

(52) U.S. Cl. ............... 514/173; 514/175
(58) Field of Classification Search ........ 514/173, 514/171
See application file for complete search history.

(56) References Cited

FOREIGN PATENT DOCUMENTS

| EP | 0 714 663 | 6/1996 |
| JP | 09 071 586 | 3/1997 |
| WO | WO 96/24373 A2 | 8/1996 |
| WO | WO 98/15267 | 4/1998 |
| WO | WO 99/02142 | 1/1999 |

OTHER PUBLICATIONS

The RALES Investigators. Effectiveness of Spironolactone added to an angiotensin-converting enzyme inhibitor and a loop diuretic for severe chronic congestive heart failure. American Journal Cardiology, vol. 78, pp. 902-907, 1996.*
Freeman et al. Nutrition Reviews, Oct. 1994. vol. 52, No. 10, pp. 340-347.*
Packer et al, New England Journal of Medicine, 1996. vol. 334, pp. 1349-1355.*
Coats, et al., "Prevention and reversal of cardiac cachexia in patients with severe heart failure by carvedilol: Results of the Copernicus study" Scientific Sessions 2001 of the American Heart Association Supplement 104(17): II-437 (2001).
Saitoh, et al., "Carteolol improves body weight and visceral fat weight gains in OLETF rats, a model of NIDDM with mild obesity" *Diabetologia*, 16th International Diabetes Federation Congress; Helsinki, Finland, Supplement 1, 40(1): A365 (1997).

Anker & Coats, "Cardiac Cachexia. A syndrome with impaired survival and immune and neuroendocrine activation," *Chest* 115:836-847 (1999).
Anker & Rauchhaus, "Insights into the pathogenesis of chronic heart failure: immune activation and cachexia," *Curr Opin Cardiol* 14(3):211-216 (1999).
Anker, "Catecholamine levels and treatment in chronic heart failure," *Eur. Heart J.* 19(Suppl F.):56-61 (1998).
Anker, "Relation between serum urice acid and lower limb blood flow in patients with chronic heart failure," *Heart* 78:39-43 (1997).
Anker, et al., "Cytokines and neurohormones relating to body composition alterations in the wasting syndrome of chronic heart failure," *European Heart Journal* 20:683-693 (1999).
Anker, et al., "Hormonal changes and catabolic/anabolic imbalance in chronic heart failure and their importance for cardiac cachexia," *Circulation* 96:526-534 (1998).
Anker, et al., "Loss of bone mineral in patients with cachexia due to chronic heart failure," *Am J Cardiol* 83:612-615 (1999).
Anker, et al., "The influence of muscle mass, strength, fatigability and blood flow on exercise capacity in cachectic and non-cachectic patients with chronic heart failure," *European Heart Journal* 18:259-269 (1997).
Anker, et al., "Tumor necrosis factor and steroid metabolism in chronic heart failure: Possible relation to muscle wasting," *J Amer Coll Cardiol* 30:997-1001 (1997).
Anker, et al., "Tumour necrosis factor alpha as a predictor of impaired peak leg blood flow in patients with chronic heart failure," *Q. J. Med.* 91:199-203 (1998).
Benedict & Grahame-Smith, "Plasma adrenaline and noradrenaline concentrations and dopamine-b-hydroxylase activity in myocardial infarction with and without cardiogenic shock," *British Heart Journal* 42:214-220 (1979).
Berne, "Effect of epinephrine and norepinephrine on coronary circulation," *Circ Res* 6:644-655 (1958).
Besarb, et al., "The effects of normal as compared with low hematocrit values in patients with cardiac disease who are receiving hemodialysis and epotein," *N Eng J Med* 339(9):584-590 (1998).

(Continued)

*Primary Examiner*—Manjunath Rao
*Assistant Examiner*—Fozia M Hamud
(74) *Attorney, Agent, or Firm*—Pabst Patent Group LLP

(57) ABSTRACT

A method of treating weight loss due to underlying disease in a patient the method comprising administering to the patient an effective amount of an agent which reduces sympathetic nervous system activity. A method of treating weight loss due to underlying disease in a patient the 10 method comprising administering to the patient an effective amount of any one or more of the following: a compound which inhibits the effect of aldosterone such as an aldosterone antagonist; a chymase inhibitor; a cathepsin B inhibitor; a 13 receptor blocker; an imidazoline receptor antagonist; a centrally acting tx receptor antagonist; a peripherally acting ct receptor antagonist; a ganglion blocking agent; a drug that has an effect on cardiovascular reflexes and thereby reduce SNS activity such as an opiate; scopolamine; an endothelin receptor antagonist; and a xanthine oxidase inhibitor. The methods are particularly useful in treating cardiac cachexia.

10 Claims, 5 Drawing Sheets

OTHER PUBLICATIONS

Brink, et al., "Angiotension II causes weight loss and decreases circulating insulin-like growth factor I in rats through a pressor-independent mechanism," *J Clin Invest* 97(11):2509-2516 (1996).

Chilain, et al., "Andrenergic coronary tone during submaximal exercise in the dog is produced by circulating catecholamines," *Cir Res* 58:68-62 (1986).

Chua, et al., "Relation between chemosensitivity and the ventilatory response to exercise in chronic heart failure," *J Am Coll Cardiol* 27:650-657 (1996).

Coats, "Symptoms and quality of life In heart failure: the muscle hypothesis," "Symptoms and quality of lifein heart failure: the muscle hypothesis," *Br. Heart J* 72:S36-S39 (1994).

Cowie, et al., "The epidemiology of heart failure," *European Heart Journal* 18:205-225 (1997).

Daneryd, et al., "Protection of metabolic and exercise capacity in unselected weight-losing cancer patients following treatment with recombinant erythropoietin: A randomized prospective study," *Cancer Res.* 58(23):5374-5379 (1998).

Davenport, "Characterization of [$^{125}$I]-PD164333, an $ET_A$ selective non-peptide radiolabelled antagonists, in normal and diseased human tissues," *Br. J Pharmacol* 123(2):223-30 (1998).

Doherty, et al., "In vitro and in vivo studies with a series of hexapeptide endothelin antagonists," *J Cardiovascular Pharmacology* 22(Suppl 8):S98-S102 (1993).

D'Uscio, et al., "Efects of chronic $ET_A$-receptor blockade in angiotension II-induced hnypertension," *Hypertension* 29(1 Pt. 2):435-41 (1997).

Francis, "Camparison of neuroendocrine activation in patients with left ventricular dysfunction with and without congestive heart failure," *Circulation* 82:1724-1729 (1990).

Gagnon & Bruera, "A review of the dug treatment of cachexia associated with cancer," *Drugs* 55(5):675-688 (1998).

Goldstein, "Plasma norepinephrine as an indicator of sympathetic neural activity in clinical cardiology," *Am J Cardiol* 48:1147-54 (1981).

Gorter, "Management of anorexia-cachexia associated with cancer and HIV infection," *Oncology* 5(9):13-17 (1991).

Greenbaum, et al., "Host cathepsin D response to tumor in the normal and pepstatin-treated mouse," *Cancer Res.* 43(6):2584-2587 (1983).

Harris,"Congestive cardiac failure: central role of the arterial blood pressure," *Br Heart J* 58:190-203 (1987).

Hashida, "Inhibitions by E-64 derivatives of rat liver cathespsin B and cathespsin L in vitro and in vivo," *J Biochem* 88:1805-1811 (1980).

Heusch & Deussen, "The effects of cardiac sympathetic nerve stimulation on perfusion of stenotic coronary arteries in the dog," *Circ Res* 53:8-15 (1983).

Heusch, "α-Adrenergic mechanisms in myocardial Ischemia," *Circulation* 81:1-13 (1990).

Huang, et al., "Antialdosterone therapy in severe chronic congestive heart failure," *Zhonghua Xinxueguanbing Zazhi* 24(1):12-15 (1996).

Ihara, et al., "In vitro biological profile of a highly potent novel endolethial (ET) antagonist BQ-123 selective for the $ET_A$ receptor," *J Cardiovasc Pharmcol* 20(Suppl. 12):S11-S14 (1992).

Ishikawa, et al., "Biochemical and pharmacological profile of a potent and selective endothelin B-receptor antagonist, BQ-788," *Proc Natl Acad Sci USA* 91:4892-4892 (1994).

Jae, et al., "Pyrrolidine-3-carboxylic acids as endothelin antagonists. 2. Sulfonamide-based $ET_A/ET_B$ mixed antagonists," *J Med Chem* 40:3217-3227 (1997).

Kalimi, et al., "Effects of antimineralocorticoid RU 26752 on steroid-induced hypertension in rats," *Am J Phusiol* 258(5, Pt 1):E737-9 (1990).

Kichuk, et al., "Angiotension-converting enzyme inhibitors promote nitric oxide production in coronary microvessels from failing explanted human hearts," *Am J Cardiol* 80:137A-142A (1997).

Kim, et al., "Evaluation of RU28318 and RU40555 as selective mineralocorticoid receptor and glucocorticoid receptor antagonists, respectively: receptor measures and functional studies," *J Steroid Biochem Mol Biol* 67(3):213-22 (1998).

Ley, et al., "Sex- and menopause-associated changed in body-fat distribution," *Am J Clin Nutr* 55:950-4 (1992).

Leza, et al., *Revista de Farmacologia Clinica y Experimental* 4/4:377-383 (1987).

Liu, et al., "Pyrrolidine-3-carboxylic acids as endothelin antagonists. 3. Discovery of a potent, 2-nonaryl, highly selective $ET_A$ antagonist (A-261546)," *J Med Chem* 41:3261-3275 (1998).

Maguire, et al., "Affinity and selectiveity of PD156707, a novel nonpeptide endothelin antagonists, for human $ET_A$ and $ET_B$ receptors," *J Pharmacol Exp Ther* 280(2):1102-8 (1997).

McDonald, et al., "Plasma-catecholamines after cardiac infarction," *Lancet* 2:1021-1023 (1969).

Mihara, et al., "Binding characterization of [$^3$H]S-0139, an antagonist of the endothelin $ET_A$ receptor subtype," *Eur J Pharmacol* 342:2-3:319-24 (1998).

Miyata, et al., "WS-7338, New endothelin receptor antagonists isolated from *Streptomyces* sp. No. 7338. II. Biological characterization and pharmacological characterization of WS-7338 B," *J Antibiot* (Tokyo) 45(1):83-7 (1992).

Mueller & Ayres, "Propranolol decreases sympathetic nervous activity reflected by plasma catecholamines during evolution of myocardial infarction in man," *J Clin Invest* 65:338-346 (1980).

Mueller, et al., "Cardiac catheolamine response during evolving myocardial infarct in man," *Circulation* 62(Suppl III):III-81 (1980).

Nambi, et al., "Nonpeptide endothelin receptor antagonists. 1. Effects on binding and signal transduction on human endothelin$_A$ and endothelin$_B$ receptors," *J Pharmacol Exp Ther* 271(2):755-61 (1994).

Nycander, et al., "Two-step mechanism of inhibition of cathespin B by cystain C due to displacement of the proteinase occluding loop," *FEBS Lett* 422:61-64 (1998).

Ohshita, et al., "Effects of selective inhibition of cathepsin B and general inhibition of cysteine proteinases on lysosomal proteolysis in rat liver in vivo and in vitro," *N Eur J Biochem* 209(1):223-31 (1992).

Packer, "The neurohormonal hypothesis: a theory to explain the mechanism of disease progression in heart failure," *J Am Coll Cardiol* 20:248-254 (1992).

Piepoli, et al., "Contribution of muscle afferents to the hemodynamic, autonomic and ventilatory responses to exercise in patients with chronic heart failure," *Circulation* 93(5):940-952 (1996).

Pomikowski, et al., "Augmented peripheral chemosensitivity as a potential input to baroreflex impairment and autonomic imbalance in chronic heart failure," *Circulation* 96(8):2586-2594 (1997).

Rahman, et al., "Angiotensin II and aldosterone have opposite effects on magnesium excretion in man," *Scot Med. J.* 37:157-158 (1992).

Remes, "Neuroendocrine activity in untreated heart failure," *Br Heart J* 65:249-255 (1991).

Roux, et al., "Ro 61-1790, a new hydrosoluble endothelin antagonist: general pharmacology and effects on experimental cerebral vasospasm," *J Pharmacol Exp Ther* 283(3):1110-18 (1997).

Sakaki, et al., "Discovery of IRL 3461: A novel and potent endothelin antagnoist with balanced $ET_A/ET_B$ affinity," *Bioorg Med Chem Lett* 8(16):2241-6 (1998).

Shen, et al., "Defective endogenous nitric oxide-mediated modulation of cellular respiration in canine skeletal muscle after the development of heart failure," *J Heart Lung Transplant* 16(10):1026-1034 (1997).

Siggers, et al., "Serial plasma adrenaline and noradrenaline levels in myocardial infarction using a new double isotope technique," 33:878-883 (1971).

Sigurdsson, et al., "Short- and long-term neurohormonal activation following acute myocardial infarction," *Am Heart J* 126:1068-1076 (1993).

Sutsch, et al., "Short-term oral endothelial-receptor antagonist therapy in conventionally treated patients with symptomatic severe chronic heart failure," *Circulation* 98(21):2262-2268 (1998).

Tasker, et al., "Potent and selective non-benzodioxole-containing endothelin-A-receptor antagonists," *J Med Chem* 40:322-330 (1997).

The SOLVD Investigators, "Effect of enalapril on survival in patients with reduced left ventricular ejection fractions and congestive heart failure," *N Eng J Med* 325:293-302 (1991).

Towatari, et al., "Novel epoxysuccinyl peptides. A selective inhibitor of cathepsin B, in vivo," *N. FEBS Lett* 280(2):311-5 (1991).

Tschesche, "Bimolecular interaction of matrix metalloproteinases and their inhibitors," *J Protein Chem* 17(6):549-51 (1998).

Turk, et al., "Identification of bovine stefin A, a novel protein inhibitor of cysteine proteinases," *FEBS Lett* 360:101-105 (1995).

Vetter, et al., "Initial metabolic and hormonal response to acute myocardial infarction," *Lancet* 1:284-289 (1974).

Weindel, et al., "Inhibitory effects of the novel anti-aidosterone compound mespirenone on adrenocortical steroidogenesis in vitro," *Arzneimittelforschung* 41(9):946-9 (1991).

Zhang, et al., "ACE inhibitors promote nitric oxide accumulation to modulate myocardial oxygen consumption," *Circulation* 95(1):176-182 (1997).

Aarsland, et al., "Beta-blockade lowers peripheral lipolysis in burn patients receiving growth hormone. Rate of hepatic very low density lipoprotein triglyceride secretion remains unchanged", *Ann. Surg.*, 223(6):777-89 (1996).

Brooks, et al., "Sympathetic activation of brown-adipose-tissue thermogenesis in cachexia", *Biosci. Rep.*, 1(6):509-17 (1981).

Coombes, et al., "Changes in thermogenesis and brown fat activity in response to tumour necrosis factor in the rat", *Biosci. Rep.*, 7(10):791-9 (1987).

Klein and Wolfe, "Whole-body lipolysis and triglyceride-fatty acid cycling in cachectic patients with esophageal cancer", *J. Clin. Invest.*, 86(5):1403-8 (1990).

Roe, et al., "Mechanisms of cachexia induced by T-cell leukemia in the rat", *Metabolism*, 45(5):645-51 (1996).

Wilmore, et al., "Catecholamines: mediator of the hypermetabolic response to thermal injury", *Ann. Surg.*, 180(4):653-69 (1974).

* cited by examiner

METHODS OF TREATING CACHEXIA

This application is a 371 of International Application No. PCT/GB99/03302 entitled "Methods of Treatment", filed in the United Kingdom Receiving Office for the PCT on Oct. 15, 1999, which claims priority to Patent Application No. 9822458.7, filed in the United Kingdom on Oct. 15, 1998, Patent Application No. 9822459.5, filed in the United Kingdom on Oct. 15, 1998, and Patent Application No. 9917181.1, filed in the United Kingdom on Jul. 23, 1999.

BACKGROUND OF THE INVENTION

The present invention relates to methods of treatment, in particular it relates to methods of treating weight loss due to underlying disease (cachexia).

Weight loss due to underlying disease, often termed "cachexia", occurs in patients with a wide variety of diseases including acquired immune deficiency syndrome (AIDS), liver cirrhosis, chronic obstructive pulmonary disease, chronic renal failure, chronic infections including pneumonia, cancer (cancer cachexia), diabetes and heart disease including hypertension and chronic heart failure (CHF) (cardiac cachexia). Cachexia may also occur idiopathically.

In all cases, cachexia may be an indicator of a poor prognosis and its reversal, stopping or at least slowing down, is desirable. Indeed, a strong relationship between weight loss and mortality has been found for many conditions.

Hormonal changes and catabolic/anabolic imbalance in chronic heart failure (CHF) and their relevance in cardiac cachexia has been discussed in Anker et al (1997) *Circulation* 96, 526-534. Similarly, catecholamine levels, serum uric acid levels, TNFα levels and other hormone levels have been measured in patients with CHF (see, for example. Anker et al (1997) *Heart* 78, 39-43; Anker et al (1998) *Q J. Med.* 91, 199-203; Anker (1998) *Eur. Heart J.* 19, (Suppl F), F56-F61; Anker et al (1497) *J. Amer. Coll. Cardiol.* 30, 997-1001; Anker et al (1999) *Eur. Heart.* 20, 683-693; Anker (1999) *Chest* 115, 836-847). In addition, studies have been made of the loss of bone mineral in patients with cachexia due to CHF (Anker et al (1999) *Am. J. Cardiol.* 83, 612-615).

BRIEF SUMMARY OF THE INVENTION

However, no-one has suggested that reducing sympathetic nervous system activity and/or improving cardiovascular reflex status would be beneficial to patients with cardiac cachexia and also to patients with cachexia due to any cause and, indeed, idiopathic cachexia.

A first aspect of the invention provides a method of treating weight loss due to underlying disease in a patient the method comprising administering to the patient an effective amount of an agent which reduces sympathetic nervous system activity and/or improves cardiovascular reflex status.

Without prejudice to further aspects of the invention and without being bound by any theories as to how the invention works, we believe that at least some of the information described in the Examples indicates that agents which inhibit sympathetic nervous system activity, either directly or indirectly, (for example by directly or indirectly having ergo-reflex, chemoreflex or baroreflex effects) have a beneficial effect on cachexia probably by a reduction of apoptosis, a reduction in metabolic rates or by vasodilation with better blood flow to tissues. We provide information that, surprisingly, certain pathways are abnormal in cachexia due to a wide range of underlying diseases, but they are not abnormal in weight loss due to starvation.

A second aspect of the invention provides a method of treating weight loss due to underlying disease in a patient the method comprising administering to the patient an effective amount of any one or more of the following: a compound which inhibits the effect of aldosterone such as an aldosterone antagonist; a chymase inhibitor; a cathepsin inhibitor; a β receptor blocker; an imidazoline receptor antagonist; a centrally acting α receptor antagonist; a peripherally acting α receptor antagonist; a ganglion blocking agent; a drug that has an effect on cardiovascular reflexes and thereby reduce SNS activity such as an opiate via chemoreceptor; scopolamine; an endothelin receptor antagonist; a xanthine oxidase inhibitor; and erythropoietin.

The method may be used on any mammal and so the term "patient" includes a human patient and also includes any other mammal including domestic animals such as cats and dogs, and farm animals such as cows, pigs, horses, sheep, goats and the like. It is preferred if the method is used to treat humans.

A third aspect of the invention provides a method of treating weight loss due to underlying disease in a patient the method comprising electrically stimulating the patient's muscles. This may be done using any transcutaneous electrical stimulator applied to the skin over a muscle or its nerve to stimulate muscle contractions. Suitably, to increase muscle strength and bulk high frequency stimulation (eg 50 Hz) is used. In contrast low frequency stimulation (eg 10 Hz) may enhance slow fatigue resistant fibres and could cause a fibre type shift which could reduce strength and so is not preferred.

In treating weight loss due to underlying disease in a patient it is useful if the weight loss is reversed or stopped or at least slowed down.

The aforementioned compounds and procedures are useful for the treatment or prevention of weight loss due to underlying disease (cachexia). These underlying diseases include, for example, but are not restricted to, AIDS, liver cirrhosis, chronic obstructive pulmonary disease with or without emphysema, chronic renal failure, chronic infections (like pneumonia), cancer (ie cancer cachexia), and heart disease including hypertension and chronic heart failure (ie cardiac cachexia), and idiopathic cachexia (ie cachexia due to unknown disease).

DETAILED DESCRIPTION OF THE INVENTION

Figure 1:
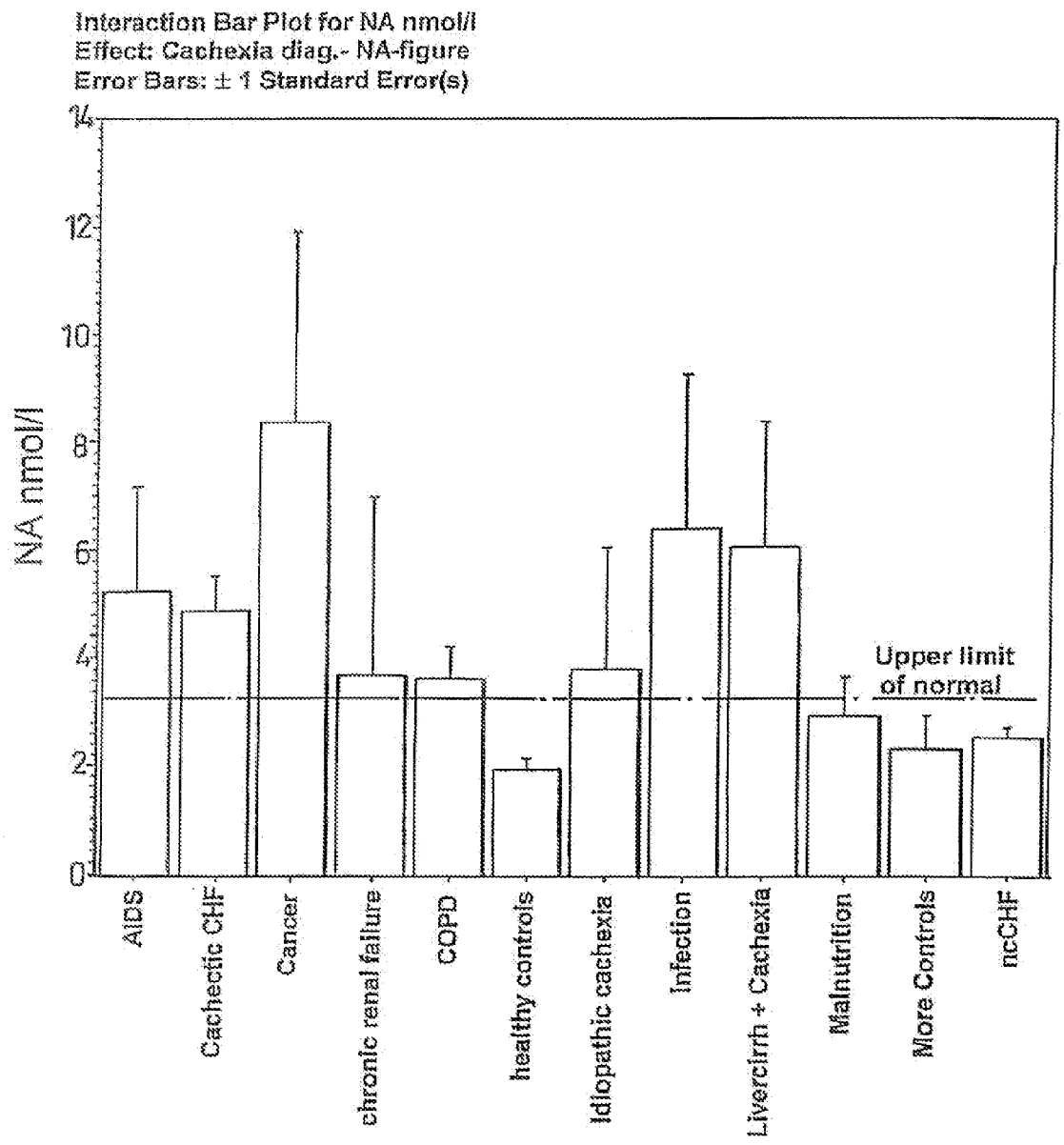
FIG. 1 shows that chronic wasting disorders show increased activity of SNS (sympathetic nervous system) as evidenced by increased plasma noradrenaline levels. All of the cachectic disorders marked (*) have mean plasma noradrenaline levels which are higher than normal. Mean values are given for noradrenaline plasma levels in nmol/l. COPD is chronic occluded pulmonary disease. ncCHF is non-cachectic CHF.
Figure 2:
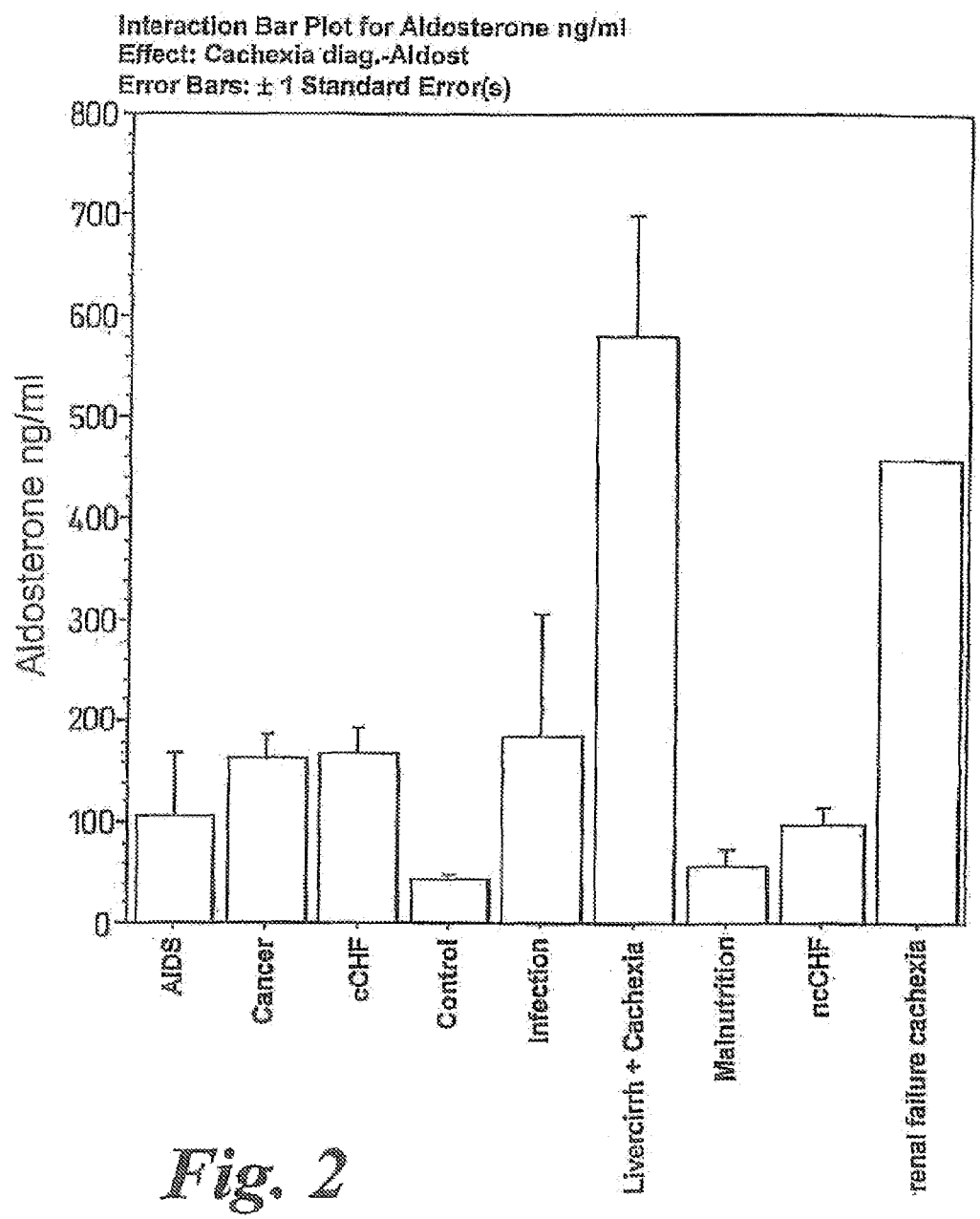
FIG. 2 shows that, on average, patients with active wasting disease have 2.5- to 12-fold increased aldosterone levels compared to healthy controls (their mean: 43.2 ng/ml, upper limit or normal: 81 ng/ml). Patients with weight loss due to malnutrition have normal aldosterone levels.

Compounds or procedures that may reduce angiotensin II plasma levels and therefore are useful in the practice of the invention include:

1. any compound with an inhibiting effect on aldosterone, eg aldosterone antagonists such as spironolactone (which may be given at between 12.5 mg and 300 mg per day, orally) and testolactone (which may be given at 40 mg/kg per day, orally), RU40555 (which may be given at 10-30 mg/kg orally), RU26752 (a synthetic aldosterone antagonist), canrenoate (which may be given at 20 mg/day iv) also known as Canrenoate Potassium, eplerenone (oral), 3-(17 beta-hydroxy-3-oxoandrosta-1,4,6,11-tetraen-17 alpha-yl)propionic acid gamma-lactone, 3-(9 alpha-fluoro-17 beta-hydroxy-3-oxoandrost-4-en-17 alpha-yl)propionic acid gamma-lactone (31), dihydrospirorenone, spirorenone, 15,16-methylene derivatives of spironolactone, mespirenone (CAS 87952-98-5) and SC9420;
2. chymase inhibitors, including alendronate, aprotinin and tissue inhibitors of matrix metalloproteinases (TIMPs);
3. cathepsin B inhibitors, including epoxysuccinyl peptides such as CA-074 and E-64c, stefinA, cystatin C (endogenous inhibitor), CA074 (a specific inhibitor of cathepsin B) and E-64 (natural inhibitor of cathepsin B);
4. exercise training;
5. electrical muscle stimulation;

Compounds that may reduce catecholamine plasma levels and the activity of the sympathetic nervous system (SNS) include:
6. Beta (β) receptor blockers including acebutolol, alprenolol, atenolol, betaxolol, bisoprolol, carteolol, celiprolol, esmolol, labetolol, lavobunolol, metipranolol, metoprolol, nadolol, oxprenolol, penbutolol, pindolol, propanolol, sotalol, nebivolol, carvedilol, bucindolol and timolol; Atenolol and bisoprolol are preferred.
7. imidazoline receptor antagonists (including moxonidine, clonidine, rilmenidine, pentamidine (1,5-bis(4-amidonophenoxy)pentane) and alpha methyl dopa;
8. centrally acting alpha receptor agonists like clonidine;
9. peripherally acting alpha receptor antagonists such as doxazosin (which may be given at 1-16 mg orally per day), prazosin, terazosin and ipsapirone;
10. ganglion blocking agents including azamethonium, dicolinium, hexamethonium, mecamylamine, pentamethonium, pentolinium, trimetaphan, benzohexonium, hexafluorenium, cypenam, trimethaphan canfosulfonate, tetraethylammonium bromide, and synapleg;
11. drugs that have effects on cardiovascular reflexes and thereby reduce SNS activity including
   opiates (via chemoreceptor) such as dihydrocodeine, morphine, diamorphine and buprenorphine
   scopolamine;
12. xanthine oxidase inhibitors including allopurinol (which may be given at 50-1000 mg per day orally), 7,8-dihydroneopterin, 5,6,7,8-tetrahydrobiopterin, leukopterin, xanthopterin, neopterin, biopterin, 4-amino-6-hydroxypyrazolo[3,4-d]pyrimidine (AHPP), and oxypurinol;
   Allopurinol is preferred.

Endothelin receptor (such as ET-I receptor) antagonists include
endothelin receptor A antagonist BQ 123
ETB-receptor antagonist BQ-788
A-216546 ([2S-(2,2-dimethylpentyl)-4S-(7-methoxy-1,3-benzodioxol-5-yl)-1-(N,N-di(n-butyl)aminocarbonyl-methyl)-pyrrolidine-3R-carboxylic acid), a potent antagonist with >25,000-fold selectivity for the endothelin ET(A) receptor
ABT-627 (1, A-147627, active enantiomer of A-127722), a 2,4-diaryl substituted pyrrolidine-3-carboxylic acid based endothelin receptor-A antagonist. This compound binds to the ETA receptor with an affinity (Ki) of 0.034 nNM and with a 2000-fold selectivity for the ETA receptor versus the ETB receptor.

IRL 3461: a potent endothelin antagonist with balanced ETA/ETB affinity
oral endothelin-receptor antagonist bosentan (0.1-1.0 g BID, preferred 0.25-0.5 g BID), has combined ETA/ETB affrnitv
LU135252, a selective antagonist of the ETA receptor
S-0139, (+)-disodium 27-[(E)-3-[2-[(E)-3-carboxylatoacryloylamino]-5-hydroxyphenl]acrylayloxy]-3-oxoolean-12-en-28-oate, an ETA selective antagonist
N-(6-(2-(5-bromopyrimidin-4-yl)-4-(2-hydroxy-1,1-dimethylethyl)-benzensulfonamide sodium salt sesquihydrate (T-0201), a nonpeptide endothelin (ET) receptor antagonist. In binding studies, T-0201 competitively antagonized the specific binding of [125I]-ET-1 to human cloned ETA receptors
unselective ET(A)/ET(B) receptor antagonist, PD 142,893
PD164333, an analogue of the orally active butenolide antagonists of the endothelin ETA receptor
Ro 61-1790 [5-methyl-pyridine-2-sulfonic acid 6-(2-hydroxy-ethoxy)-5-(2-methoxy-phenoxy)-2-(2-1H-tetrazol-5-yl-+++pyridin-4-yl)-pyrimidin-4-ylamide] is a competitive ET antagonist with an affinity to ETA receptor in the subnanomolar range. It has an approximately 1000-fold selectivity for the ETA vs the ETB receptor
ET-A antagonist PD-156,707
SB 209670, a rationally designed potent nonpeptide endothelin receptor antagonist
endothelin B receptor-selective antagonist: IRL 1038, [Cys11-Cys15]-endothelin-1 (11-21)
WS-7338 B, a specific antagonist for vascular ETA receptors.

The endothelins (ETs) are a family of bicyclic 21-amino acid peptides that are potent and prolonged vasoconstrictors. ET receptor antagonists improve peripheral blood flow, improve muscle metabolic status and thereby ergoreflex, and, we believe, thereby reduce SNS activity. ET-A receptor blockade is preferred in the practice of the invention.

Various compounds are described in at least the following publications:

RU40555
Evaluation of RU28318 and RU40555 as selective mineralocorticoid receptor and glucocorticoid receptor antagonists, respectively: receptor measures and functional studies. Kim P J, Cole M A, Kalman B A, Spencer R L. *J Steroid Biochem Mol Biol* 1998 Nov 67: 3 213-22.

RU 26752
Effects of antimineralocorticoid RU 26752 on steroid-induced hypertension in rats. Kalimi M, Opoku J, Agarwal M, Corley K. *Am J Physiol* 1990 May 258: 5 Pt 1 E737-9.

CAS 87952-98-5
Inhibitory effects of the novel anti-aldosterone compound mespirenone on adrenocortical steroidogenesis in vitro. Weindel K, Lewicka S, Vecsei P. *Arzneimittelforschung* 1991 Sep 41: 9 946-9.

SC9420
Blocking by spironolactone (SC 9420) of the action of aldosterone upon the intestinal transport of potassium, sodium, and water. Elmslie R G, Mulholland A T, Shields R. *Gut* 1966 Dec. 7: 6 697-9.

TIMPS
Bimolecular interaction of matrix metalloproteinases and their inhibitors TIMPs. Tschesche H. *J Protein Chem* 1998 Aug. 17: 6 549-51.

CA-074
Novel epoxysuccinyl peptides. A selective inhibitor of cathepsin B, in vivo. Towatari T, Nikawa T, Murata M, Yokoo C, Tamai M, Hanada K, Katunuma N. *FEBS Lett* 1991 Mar. 25 280: 2 311-5.

E-64c
Effects of selective inhibition of cathepsin B and general inhibition of cysteine proteinases on lysosomal proteolysis in rat liver in vivo and in vitro. Ohshita T, Nikawa T, Towatari T, Katunuma N. *Eur J Biocliem* 1992 Oct. 1 209: 1 223-31.

Stefin A
Identification of bovine stefin A, a novel protein inhibitor of cysteine proteinases. Turk B, Ritonja A, Björk I, Stoka V, Dolenc I, Turk V. *FEBS Lett* 1995 Feb. 27 360: 2 101-5.

cystatin C
Two-step mechanism of inhibition of cathepsin B by cystatin C due to displacement of the proteinase occluding loop. Nycander M, Estrada S, Mort J S, Abrahamson M, Björk I. *FEBS Lett* 1998 Jan. 23 422: 1 61-4.

E64
Inhibitions by E-64 derivatives of rat liver cathepsin B and cathepsin L in vitro and in vivo. Hashida S, Towatari T, Kominami E, Katunuma N. J Biochem (Tokyo) 1980 Dec 88: 6 1805-11.

BQ 123
In vitro biological profile of a highly potent novel endothelin (ET) antagonist BQ-123 selective for the ETA receptor. Ihara M, Ishikawa K, Fukuroda T, Saeki T, Funabashi K, Fukami T, Suda H, Yano M. *J Cardiovasc Pharmacol* 1992 20 Suppl 12 S11-4.

BQ-788
Biochemical and pharmacological profile of a potent and selective endothelin B-receptor antagonist, BQ-788. Ishikawa K, Ihara M, Noguchi K, Mase T, Mino N, Saeki T, Fukuroda T, Fukami T, Ozaki S, Nagase T, et al. *Proc Natl Acad Sci USA* 1994 May 24 91: 11 4892-6.

A-216546
Pyrrolidine-3-carboxylic acids as endothelin antagonists. 3. Discovery of a potent, 2-nonaryl, highly selective ETA antagonist (A-216546). Liu G, Henry K J Jr, Szczepankiewicz B G, Winn M, Kozmina N S, Boyd S A, Wasicak J, von Geldern T W, Wu-Wong J R, Chiou W J, Dixon D B, Nguyen B, Marsh K C, Opgenorth T J. *J Med Chem* 1998 Aug. 13 41: 17 3261-75.

A-127722
Potent and selective non-benzodioxole-containing endothelin-A receptor antagonists. Tasker A, Sorensen B K, Jae H S, Winn M, von Geldern T W, Dixon D B, Chiou W J, Dayton B D, Calzadila S, Hernandez L, Marsh K C, WuWong J R, Opgenorth T J. *J Med Chem* 1997 Jan. 31 40: 3 322-30.

ABT-627
Pyrrolidine-3-carboxylic acids as endothelin antagonists. 2. Sulfonamide-based ETA/ETB mixed antagonists. Jae H S, Winn M, Dixon D B, Marsh K C, Nguyen B, Opgenorth T J, von Geldern T W. *J Med Chem* 1997 Sep. 26 40: 20 3217-27.

IRL 3461
Discovery of IRL 3461: a novel and potent endothelin antagonist with balanced ETA/ETB affinity. Sakaki J, Murata T, Yuumoto Y, Nakamura I, Trueh T, Pitterna T, Iwasaki G, Oda K, Yamamura T, Hayakawa K. *Bioorg Med Chem Lett* 1998 Aug. 18 8: 16 2241-6.

LU135252
Effects of chronic ETA-receptor blockade in angiotensin II-induced hypertension. d'Uscio L V, Moreau P, Shaw S, Takase H, Barton M, Lüscher T F. *Hypertension* 1997 Jan. 29: 1 Pt 2 435-41.

S-0139
Binding characterization of [3H]S-0139, an antagonist of the endothelin ET(A) receptor subtype. Mihara S, Tozawa F, Itazaki K, Fujimoto M. *Eur J Pharmacol* 1998 Jan. 26 342: 2-3 319-24.

T-0201
Pharmacological profile of T-0201, a highly potent and orally active endothelin receptor antagonist. Hoshino T, Yamauchi R, Kikkawa K, Yabana H, Murata S. *Pharmacol Exp Ther* 1998 Aug 286: 2 643-9.

PD 142, 893
In vitro and in vivo studies with a series of hexapeptide endothelin antagonists. Doherty A M, Cody W L, He J X, DePue P L, Cheng X M, Welch K M, Flynn M A, Reynolds E E, LaDouceur D M, Davis L S, et al. *J Cardiovasc Pharmacol* 1993 22 Suppl 8 S98-102.

PD164333
Characterization of [$^{25}$I]-PD164333, an ETA selective non-peptide radiolabelled antagonist, in normal and diseased human tissues. Davenport A P, Kuc R E, Ashby M J, Patt W C, Doherty A M. *Br J Pharmacol* 1998 Jan 123: 2 223-30.

Ro 61-1790
Ro 61-1790, a new hydrosoluble endothelin antagonist: general pharmacology and effects on experimental cerebral vasospasm. Roux S, Breu V, Giller T, Neidhart W, Ramuz H, Coassolo P, Clozel J P, Clozel M. *J Pharmacol Exp Ther* 1997 Dec 283: 3 1110-8.

PD 156707
Affinity and selectivity of PD156707, a novel nonpeptide endothelin antagonist, for human ET(A) and ET(B) receptors. Maguire J J, Kuc R E, Davenport A P. *J Pharmacol Exp Ther* 1997 Feb 280: 2 1102-8.

SB209670
Nonpeptide endothelin receptor antagonists. I. Effects on binding and signal transduction on human endothelinA and endothelinB receptors. Nambi P, Elshourbagy N, Wu H L, Pullen M, Ohlstein E H, Brooks D P, Lago M A, Elliott J D. Gleason J G, Ruffolo R R Jr. *J Pharmacol Exp Ther* 1994 Nov 271: 2 755-61.

WS-7338
WS-7338, new endothelin receptor antagonists isolated from Streptomyces sp. No. 7338. II. Biological characterization and pharmacological characterization of WS-7338 B. Miyata S, Hashimoto M, Fujie K, Nishikawa M, Kiyoto S, Okuhara M, Kohsaka M. *J Antibiot (Tokyo)* 1992 Jan 45: 1 83-7.

Erythropoietin may be any suitable form of erythropoietin. Typically, when the patient to be treated is a human, the erythropoietin is recombinant human erythropoietin (rhEPO).

Without prejudice to any aspect of the invention, and without being bound by any theory concerning the way the invention works, we believe that EPO improves oxygen delivery to muscle which leads to a better muscle metabolic state which decrease ergoreflex and improves cachexia.

Without prejudice to any aspect of the invention and without being bound by any theory concerning the way the invention works, we believe that administration of opiate agents will suppress firing of the arterial chemoreflexes and via this action will inhibit sympathetic nervous system activity and via this action will delay the progression of cachexia.

Without prejudice to any aspect of the invention, and without being bound by any theory concerning the way the invention works, we believe that scopolamine enhances baroreflex activity and by specific enhancement of vagal activity will via this action inhibit sympathetic nervous system activity and via this action will delay the progression of cachexia.

Without prejudice to any aspect of the invention, and without being bound by any theory concerning the way the invention works, we believe that aldosterone antagonists may present or reduce myocardial and skeletal muscle fibrosis which enables muscle to act more efficiently and thereby prevent or reduce the stimulus for SNS reflex abnormalities.

The above-mentioned classes of compounds and procedures are also useful in the treatment or prevention of weight loss due to the ageing process. They, as well as others mentioned below, are also useful in the enhancement of exercise performance in health.

Thus, a fourth aspect of the invention provides a method of treating or preventing weight loss due to the ageing process in a patient the method comprising administering to the patient an effective amount of an agent which reduces sympathetic nervous system activity.

A fifth aspect of the invention provides a method of treating or preventing weight loss due to the ageing process in a patient the method comprising administering to the patient an effective amount of any one or more of a compound which inhibits the effect of aldosterone such as an aldosterone antagonist; a chymase inhibitor; a cathepsin inhibitor; a β receptor blocker; an imidazoline receptor antagonist; a centrally acting α receptor antagonist; a peripherally acting a receptor antagonist; a ganglion blocking agent; a drug that has an effect on cardiovascular reflexes and thereby reduce SNS activity such as an opiate via chemoreceptor, a digitalis alkaloid via enhancement of baroreflex sensitivity; scopolamine; an ET-1 receptor antagonist; an xanthine oxidase inhibitor; and erythropoietin.

Without prejudice to any aspect of the invention, and without being bound by any theory concerning the way the invention works, we believe that digitalis alkaloids will, via increasing sensitivity of the arterial baroreflexes, inhibit sympathetic nervous system activity and, by this action, delay the weight loss.

A sixth aspect of the invention provides a method of treating or preventing weight loss due to the ageing process in a patient the method comprising electrically stimulating the patient's muscles. Typically, the patient to be treated is >65 years old. An overview about human weight homeostasis and weight loss due to ageing is given in Anker et al (1999) *Chest* 115, 836-847.

A seventh aspect of the invention provides a method of enhancing exercise performance in a healthy individual the method comprising administering to the individual an effective amount of any one or more of a compound which inhibits the effect of aldosterone such as an aldosterone antagonist; a chymase inhibitor; a cathepsin inhibitor; a β receptor blocker; an imidazoline receptor antagonist; a centrally acting α receptor antagonist; a peripherally acting α receptor antagonist; a ganglion blocking agent; a drug that has an effect on cardiovascular reflexes and thereby reduce SNS activity such as an opiate via chemoreceptor, a digitalis alkaloid via enhancement of baroreflex sensitivity, scopolamine, or an anabolic growth factor like growth hormone and insulin-like growth factor-I (IGF-I) via effects on metabo-ergoreceptor; an ET-1 receptor antagonist; a TNFα antagonist; an xanthine oxidase inhibitor; and erythropoietin, and an eighth aspect of the invention provides a method of enhancing exercise performance in a healthy patient the method comprising electrically stimulating the patient's muscles.

Similarly, without prejudice and without being bound by any theory, we believe that anabolic growth factors and insulin growth factor-1 may increase skeletal muscle bulk and reduce the metabolic stress in a given muscle on exercise which will produce less stimulation of the work-sensitive muscle ergoreceptors (metaboreceptors) and will via this action inhibit sympathetic nervous system activity and via this action will delay the progression of cachexia.

Suitable digitalis alkaloids include digoxin and digitoxin and are believed to work in the context of the invention via enhancement of baroreflex sensitivity.

Suitable anabolic growth factors include growth hormone and insulin-like growth factor-I, and are believed to act via effects on the metabo-ergoreceptor.

By "TNFα antagonists" we mean any agent which blocks the activity of TNFα. Such antagonists include anti-TNFα antibodies and suitable forms of TNFα receptor (eg soluble forms) that bind to TNFαc and render TNFα molecules to be biologically less active.

Furthermore, the classes of compounds described in numbered groups 1, and 6 to 10 are also useful in preventing weight loss consequent to cardiovascular disorders in patients at risk of heart disease including hypertension, dyslipidaemia and diabetes.

Thus, a ninth aspect of the invention provides a method of preventing weight loss consequent to a cardiovascular disorder in a patient at risk of heart disease the method comprising administering to the patient an effective amount of any one or more of a compound with an inhibiting effect on aldosterone; a β-receptor blocker; an imidazoline receptor antagonist; a centrally acting α receptor agonist, a peripherally acting a receptor antagonist; and a ganglion blocking agent.

The drugs are administered to the patient in any suitable form or by any suitable route in order to have the desired effect. The invention also includes the use of the drug in the manufacture of a medicament for treating the patient as said.

The aforementioned compounds for use in the methods of the invention or a formulation thereof may be administered by any conventional method including oral and parenteral (eg subcutaneous or intramuscular or intravenous) injection and inhaled and per-rectal and buccal. The treatment may consist of a single dose or a plurality of doses over a period of time.

Whilst it is possible for a compound for use in the methods of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

As noted above, the compounds for use in the methods of the invention may be formulated for use. The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for parenteral including intravenous administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

Typically, the drug is administered when cachexia is diagnosed (duration of treatment: for the lifetime of the patient) or if a patient is thought to be at risk of developing cachexia. The drug is administered at a frequency and in sufficient amount to maintain trough levels of the agent at about 50% of peak dosing levels.

Other drugs which may be suitable in the practice of the invention as discussed above are known in the art; some of these compounds are listed for example in the latest editions of the British National Formulary and in the latest edition of Martindale's Pharmacoepia.

The invention will now be described in more detail with reference to the following Examples and Figures wherein Tables A, B and C show individual data for noradrenaline plasma levels which is summarised in FIG. 1.

EXAMPLE 1

Catecholamines in Chronic Heart Failure Patients

Noradrenaline Plasma Levels in Chronic Heart Failure Patients

Chronic heart failure (CHF) is a complex disorder affecting an increasing number of patients in the community with a prevalence of 10 to 30% in people over the age of 65 years [Cowie M R, Mostered A A, Wood D A, Deckers J W, Poole-Wilson P A, Sutton G C, Grobbee D E. The epidemiology of heart failure. *Europ Heart J* 1997; 18: 208-225.]. Multiple physiological pathways are pathologically affected, and a series of vicious cycles have been suggested that could transform cardiac abnormalities into haemodynamic, endocrine, immunological, and muscular abnormalities that all contribute to the clinical picture of chronic heart failure [Packer M. The neurohormonal hypothesis: A theory to explain the mechanism of disease progression in heart failure. *J Am Coll Cardiol* 1992; 20: 248-254; Anker S D, Clark A L, Kemp M, Salsbury C, Teixeira M M, Hellewell P G, Coats A J S. Tumor necrosis factor and steroid metabolism in chronic heart failure: possible relation to muscle wasting. *J Am Coll Cardiol* 1997; 30: 997-1001; Coats AJS, Clark A L, Piepoli M, Volterrani M, Poole-Wilson P A. Symptoms and quality of life in heart failure; the muscle hypothesis. *Br Heart J* 1994; 72: S36-S39.]. One of the most studied aspects is activation of the sympathetic nervous system (SNS). Activation of the SNS can be expressed in several different ways. Apart from measuring circulating catecholamines (particularly noradrenaline, adrenaline, and dopamine), it is possible to assess sympathetic nervous excitation directly by measuring nerve impulses [Van de Borne P, Montano N, Zimmerman B, Pagani M, Somers V K. Relationship between repeated measures of hemodynamics, muscle sympathetic nerve activity, and their spectral oscillations. *Circulation* 1997; 96: 4326-4332.], or indirectly by analysing heart rate and blood pressure variability [Ponikowski P, Anker S D, Chua T P, Szelemej R, Piepoli M, Adamopoulos S, Webb-Peploe K, Harrington D, Banasiak W, Wrabec K, Coats A J S. Depressed heart rate variability as an independent predictor of death in patients with chronic heart failure. *Am J Cardiol* 1997; 79: 1645-1650]. The technique of assessing catecholamine levels has also been developed further by assessing the catecholamine spill-over using radio-labelled tracers [Coats Adamopoulos S, Radelli A, McCance A, Meyer T E, Bernardi L, Solda P L, Davey P, Ormerod O, Forfar C, Conway J, Sleight P. Controlled trial of physical training in chronic heart failure: exercise performance, hemodynamics, ventilation, and autonomic function. *Circulation* 1992; 85: 2119-2131.]. Nevertheless, measurement of catecholamine levels at rest are the most widely used technique. In this respect it is important to note, that noradrenaline and adrenaline are not only released from the adrenal medulla (as hormones), but that they are also neurotransmitters that are released into the synaptic cleft of sympathetic post-ganglionic nerves (therefore also termed adrenergic). Only a small proportion of the synaptically released catecholamines spills over into the circulation. Therefore measured plasma concentrations of noradrenaline and adrenaline may in some circumstances grossly underestimate the local catecholamine concentration in the adrenergic synapses.

Catecholamines: from Myocardial Infarction to Heart Failure

Sympathetic activation is well recognised to be important contributing to the development of myocardial ischaemia [Heusch G. α-Adrenergic mechanisms in myocardial ischaemia. *Circulation* 1990; 81: 1-13.]. Cardiac β-receptors mediate increases of heart rate and inotropy, that under normal conditions lead to coronary dilation to match the oxygen demand. The direct effect of catecholamines on the coronary blood vessel is vasoconstriction mediated via α-adrenoreceptors [Berne R M. Effect of epinephrine and norepinephrine on coronary circulation. *Circ Res* 1958; 6: 644-655.]. During exercise catecholaminergic vasoconstriction is mainly mediated through circulating catecholamines and not through local hormone release [Chilian W M, Harrison D G, Haws C W, Snyder W D, Marcus M L. Adrenergic coronary tone during submaximal exercise in the dog is produced by circulating catecholamines. Evidence for adrenergic denervation supersensitivity in the myocardium but not in coronary vessels. *Circ Res* 1986; 58: 68-82.]. After the development of coronary plaques and stenosis, the vasodilatory flow reserve is reduced and the metabolic vasodilation is more and more reduced as a result of α-adrenergic coronary vasoconstriction [Heusch G, Deussen A. The effects of cardiac sympathetic nerve stimulationon the perfusion of stenotic coronary arteries in the dog. *Circ Res* 1983; 53: 8-15.].

Dramatic increases of catecholamine levels have been detected early after the onset of infarction in a variety of studies. Alone between 1969 and 1980, 15 studies with about 25000 patients and 5000 control subjects (see overview in [Goldstein DS. Plasma noradrenaline as an indicator of sympathetic neutral activity in clinical cardiology. *Am J Cardiol* 1981; 48: 1147-1154.]) have investigated plasma noradrenaline levels after myocardial infarction. Catecholamine levels peak within minutes to few hours after the onset of symptoms, and they continue to be raised for several days. The degree of the enzymatic changes during the myocardial infarction [Vetter N J, Adams W, Strange R C, Oliver M F. Initial metabolic and hormonal response to acute myocardial infarction. *Lancet* 1974; 1: 284-289.], ie severity of the heart attack, the early onset of ventricular arrhythmias [McDonald L, Baker C, Bray C, McDonald A, Restieaux N. Plasma-catecholamines after myocardial infarction. *Lancet* 1969; 2: 1021-1023.], the development of cardiogenic shock [Benedict C R, Grahame-Smith D G. Plasma adrenaline concentrations and dopamine-beta-hydrolase activity in myocardial infarction with and without cardiogenic shock. *Br Heart J* 1979; 42: 214-220.], and of congestive heart failure [McDonald et al (1969) *Lancet* 2:1021-1023; Siggers D C M, Salter C, Fluck D C. Serial plasma adrenaline and noradrenaline levels in myocardial infarction using a new double isotope technique. *Br Heart J* 1971; 33: 878-883.] are all related to plasma catecholamine levels. In patients with myocardial infarction and clinical heart failure noradrenaline remains elevated for about 1 month [Sigurdsson A, Held P, Swedberg K. Short- and long-term neurohormonal activation following acute myocardial infarction. *Am Heart J* 1993; 126: 1068-1076.]. Sedative treatment with morphines [Mueller H S. Gory D J, Rao P S, Mudd G, Ayres S M. Cardiac catecholamine response during evolving myocardial infarct in man. *Circulation* 1980 (Suppl III); 62: III-81. (abstract)], and β-blockers [Mueller H S, Ayres S M. Propranolol decreases sympathetic nervous activity reflected by plasma catecholamines during evolution of myocardial infarction in man. *J Clin Invest* 1980; 65: 338-346.] have long been known to be able to reduce catecholamine levels during acute myocardial infarction. Ischaemic heart disease is the most common cause of developing CHF.

When heart failure has fully developed it is then difficult to establish what exactly induces neurohormonal activation, as both the underlying disease process itself and the medication contribute to the complex hormonal alterations. Measurements in untreated patients have revealed that the sympathetic system is activated (raised catecholamine levels), but that in contrast the renin-angiotensin system is usually not activated [Francis G S, Benedict C, Johnstone D E, Kirlin P C, Nicklas J, Liang C S, Kubo S H, Rudin-Toretsky E, Yusuf S. Comparison of neuroendocrine activation in patients with left ventricular dysfunction with and without congestive heart failure. A substudy of the Studies of Left Ventricular Dysfunction (SOLVD). *Circulation* 1990; 82: 1724-1729; Remes J, Tikkanen I, Fyhrquist F, Pyorala K. Neuroendocrine activity in untreated heart failure. *Br Heart J* 1991; 65: 249-255.]. The initial sensor to activate these alterations remains unclear, but it is known that in the absence of a neurohormonal body response the blood pressure would fall, ie tissue blood perfusion would be insufficient [Harris P. Congestive cardiac failure: central role of the arterial blood pressure. *Br Heart J* 1987; 58: 190-203.]. Therefore the initial triggers of neurohormonal activation in heart failure could be baroreceptors in the heart and aorta. When heart failure progresses other mechanisms may gain more importance. The baroreflex responses are blunted in stable chronic heart failure, whereas the peripheral and central chemoreflex sensitivity [Pomikowski P, Chua TP, Piepoli M, Ondusova D, Webb-Peploe K, Harrington D, Anker S D, Volterrani M, Colombo R, Mazzuero G, Giordano A, Coats A J. Augmented peripheral chemosensitivity as a potential input to baroreflex impairment and autonomic imbalance in chronic heat failure. *Circulation* 1997 Oct. 21; 96(8): 2586-2594; Chua T P, Clark A L, Amadi A A, Coats A J. Relation between chemosensitivity and the ventilatory response to exercise in chronic heart failure. *J Am Coll Cardiol* 1996; 27: 650-657.] as well as the metabo-ergoreceptor reflex (afferents sensitive to skeletal muscle work load) [Piepoli M, Clark A L, Volterrani M, Adamopoulos S, Sleight P, Coats A J. Contribution of muscle afferents to the hemodynamic, autonomic, and ventilatory responses to exercise in patients with chronic heart failure: effects of physical training. *Circulation* 1996 Mar. 1; 93(5): 940-952.] deliver a strong sympathetic nervous input that may finally also lead to chronically raised catecholamine levels in sever chronic heart failure.

Catecholamines and Weight Loss in Chf Patients

Only recently, we have documented [Anker S D, Chua T P, Swan J W, Ponikowski P, Harrington D, Kox W J, Poole-Wilson P A, Coats A J S. Hormonal changes and catabolic/anabolic imbalance in chronic heart failure: The importance for cardiac cachexia. *Circulation* 1997; 96: 526-534.] that, when considering the conventional disease severity markers peak oxygen consumption, left ventricular ejection fraction (LVEF), and NYHA class, none of these markers very strongly related to resting noradrenaline and adrenaline levels. However, the presence of cardiac cachexia, ie significant non-intentional non-oedematous weight loss (>7.5% of the previous normal weight), related closely to the presence of raised catecholamine levels. Non-cachectic patients with CHF did on average not have elevated catecholamine levels.

Catecholamines can alter the metabolic status of the body, ie they can contribute to increased metabolic rates that may finally lead to a catabolic status and weight loss. This has never been considered to be a basic mechanism for body wasting in human disease in general.

Catecholamines and Weight Loss in Wasting Disorders

We have studied a variety of other cachectic conditions—for instance due to AIDS, liver cirrhosis, chronic obstructive pulmonary disease, chronic renal failure, chronic infections (like pneumonia) and cancer—and we have found activation of the SNS as evidenced by elevated plasma noradrenaline levels (mean plasma levels were clearly above the upper limit of the normal range, see Tables A, B and C and FIG. 1). This is not dependent on any specific etiology for the cachectic disorder, in fact we find elevated noradrenaline plasma levels (ie SNS activity) also in cases of idiopathic cachexia, ie cachexia of unknown origin. Nevertheless, we find the activation of the SNS to be specific for cachectic disorders, as it is not seen in patients with a similar degree of weight loss consequent upon malnutrition.

Method to Measure Noradrenaline:

Blood samples were collected after supine rest of at least 10 minutes. An antecubital polyethylene catheter was inserted and 10 ml of venous blood were drawn. After immediate centrifugation aliquots (EDTA plasma sample) were stored at −70° C. until analysis. Noradrenaline was measured by reverse-phase high pressure liquid chromatography (HPLC) with electrochemical detection. The detectable limit was: 0.2 nmol/l. The within batch coefficient of variance of repeated measures is less than 5%, the between batch coefficient of variance for repeated measures is 9%. The upper limit of normal for subjects (mean+2 standard deviations of control group: 3.31 nmnol/l).

TABLE A

ANOVA Table for NA* nmol/l

|  | DF | Sum of Squares | Mean Square | F-Value | P-Value |
|---|---|---|---|---|---|
| Cachexia diag.-NA-Figure | 11 | 260.240 | 23.658 | 2.850 | .0020 |
| Residual | 103 | 825.866 | 8.019 |  |  |

*NA is noradrenaline.

TABLE B

Means Table for NA* nmol/l
Effect: Cachexia diag.-NA*-Figure

|  | Count | Mean | Std. Dev. | Std. Err. |
|---|---|---|---|---|
| AIDS | 6 | 5.217 | 4.801 | 1.960 |
| cachectic CHF | 15 | 4.870 | 2.518 | .650 |
| Cancer | 2 | 8.365 | 5.056 | 3.575 |
| chronic renal failure | 2 | 3.686 | 4.688 | 3.315 |
| COPD | 14 | 3.643 | 2.305 | .616 |
| healthy controls | 16 | 1.940 | .687 | .172 |
| ideopathic cachexia | 2 | 3.835 | 3.203 | 2.265 |
| infection | 6 | 6.437 | 6.966 | 2.844 |
| Livercirrh + Cachexia | 6 | 6.098 | 5.693 | 2.324 |
| Malnutrition | 5 | 2.967 | 1.764 | .728 |
| more Controls | 3 | 2.373 | 1.088 | .634 |
| nc CHF | 37 | 2.684 | 1.344 | .221 |

*NA is noradrenaline.

TABLE C

Fisher's PLSO for NA* nmol/l
Effect: Cachexia diag.-NA*-Figure
Significance Level: 5%

|  | Means Diff. | Crit. Diff. | P-Value |
|---|---|---|---|
| AIDS, cachectin CHF | .347 | 2.718 | .8004 |
| AIDS, Cancer | −3.148 | 4.586 | .1768 |
| AIDS, chronic renal failure | 1.522 | 4.586 | .5118 |
| AIDS, COPD | 1.574 | 2.740 | .2579 |
| AIDS, healthy controls | 3.277 | 2.688 | .0174 |
| AIDS, ideopathic cachexia | 1.382 | 4.586 | .5514 |
| AIDS, infection | −1.220 | 3.249 | .4572 |
| AIDS, Livercirrh + Cachexia | −.882 | 3.243 | .5909 |
| AIDS, Malnutrition | 2.230 | 3.249 | .1756 |
| AIDS, more Controls | 2.643 | 3.971 | .1586 |
| AIDS, nc CHF | 2.693 | 2.472 | .0371 |
| cachectic CHF, Cancer | −3.495 | 4.228 | .1042 |
| cachectic CHF, chronic renal failure | 1.175 | 4.226 | .5827 |
| cachectic CHF, COPD | 1.227 | 2.087 | .2462 |
| cachectic CHF, healthy controls | 2.930 | 2.018 | .0049 |
| cachectic CHF, ideopathic cachexia | 1.095 | 4.228 | .6283 |
| canhectic CHF, infection | −1.667 | 2.713 | .2547 |
| cachectic CHF, Livercirrh + Cachexia | −1.228 | 2.713 | .3713 |
| cachectic CHF, Malnutrition | −1.869 | 2.713 | .1716 |
| cachectic CHF, more Controls | 2.497 | 3.552 | .1663 |
| cachectic CHF, nc CHF | 2.286 | 1.719 | .0096 |
| Cancer, chronic renal failure | 4.670 | 5.616 | .1022 |
| Cancer, COPD | 4.722 | 4.246 | .0296 |
| Cancer, healthy controls | 6.425 | 4.212 | .0031 |
| Cancer, ideopathic cachexia |  |  |  |
| Cancer, infection | 1.928 | 4.586 | .4062 |
| Cancer, Livercirrh + Cachexia | 2.267 | 4.586 | .3292 |
| Cancer, Malnutrition | 5.378 | 4.586 | .0220 |
| Cancer, more Controls | 5.992 | 5.127 | .0224 |
| Cancer, nc CHF | 5.781 | 4.077 | .0058 |
| chronic renal failure, COPD | .052 | 4.246 | .9805 |
| chronic renal failure, healthy controls | 1.755 | 4.212 | .4105 |
| chronic renal failure, ideopathic cachexia | −.140 | 5.516 | .9607 |
| chronic renal failure, infection | −2.742 | 4.586 | .2384 |
| chronic renal failure, Livercirrh + Cachexia | −2.403 | 4.586 | .3010 |
| chronic renal failure, Malnutrition | .708 | 4.586 | .7600 |
| chronic renal failure, more Controls | 1.322 | 5.127 | .6109 |
| chronic renal failure, nc CHF | 1.111 | 4.077 | .5900 |
| COPD, healthy controls | 1.703 | 2.066 | .1085 |
| COPD, ideopathic cachexia | −.192 | 4.246 | .9285 |
| COPD, Infection | −2.794 | 2.740 | .0456 |
| COPD, Livercirrh + Cachexia | −2.456 | 2.740 | .0785 |
| COPD, Malnutrition | .856 | 2.740 | .6360 |
| COPD, more Controls | 1.269 | 9.573 | .4827 |
| COPD, nc CHF | 1.059 | 1.762 | .2362 |
| healthy controls, ideopathic cachexia | −1.895 | 4.212 | .3743 |
| healthy controls, infection | −4.497 | 2.689 | .0013 |
| healthy controls, Livercirrh + Cachexia | −4.158 | 2.689 | .0028 |
| healthy controls, Malnutrition | −1.047 | 2.689 | .4418 |
| healthy controls, more Controls | −.433 | 3.533 | .8083 |
| healthy controls, nc CHF | −.644 | 1.680 | .4491 |
| ideopathic cachexia, infection | −2.602 | 4.586 | .2631 |
| ideopathic cachexia, Livercirrh + Cachexia | −2.263 | 4.586 | .3299 |
| ideopatbic cachexia, Malnutrition | .846 | 4.586 | .7144 |
| ideopathic cachexia, more Controls | 1.462 | 6.127 | .5730 |
| ideopathic cachexia, nc CHF | 1.251 | 4.077 | .5441 |
| infection, Livercirrh + Cachexia | .388 | 3.243 | .8366 |
| infection, Malnutrition | 3.450 | 3.243 | .0373 |
| infection, more Controls | 4.068 | 3.971 | .0450 |
| infection, nc CHF | 3.853 | 2.472 | .0026 |
| Livercirrh + Cachexia, Malnutrition | 3.112 | 3.243 | .0598 |
| Livercirrh + Cachexia, more Controls | 3.725 | 3.971 | .0657 |
| Livercirrh + Cachexia, nc CHF | 3.515 | 2.472 | .0058 |
| Malnutrition, more Controls | .613 | 3.971 | .7600 |
| Malnutrition, nc CHF | .403 | 2.472 | .7472 |
| more Controls, nc CHF | −.210 | 3.371 | .9017 |

*NA is noradrenaline.

EXAMPLE 2

Figure 3:
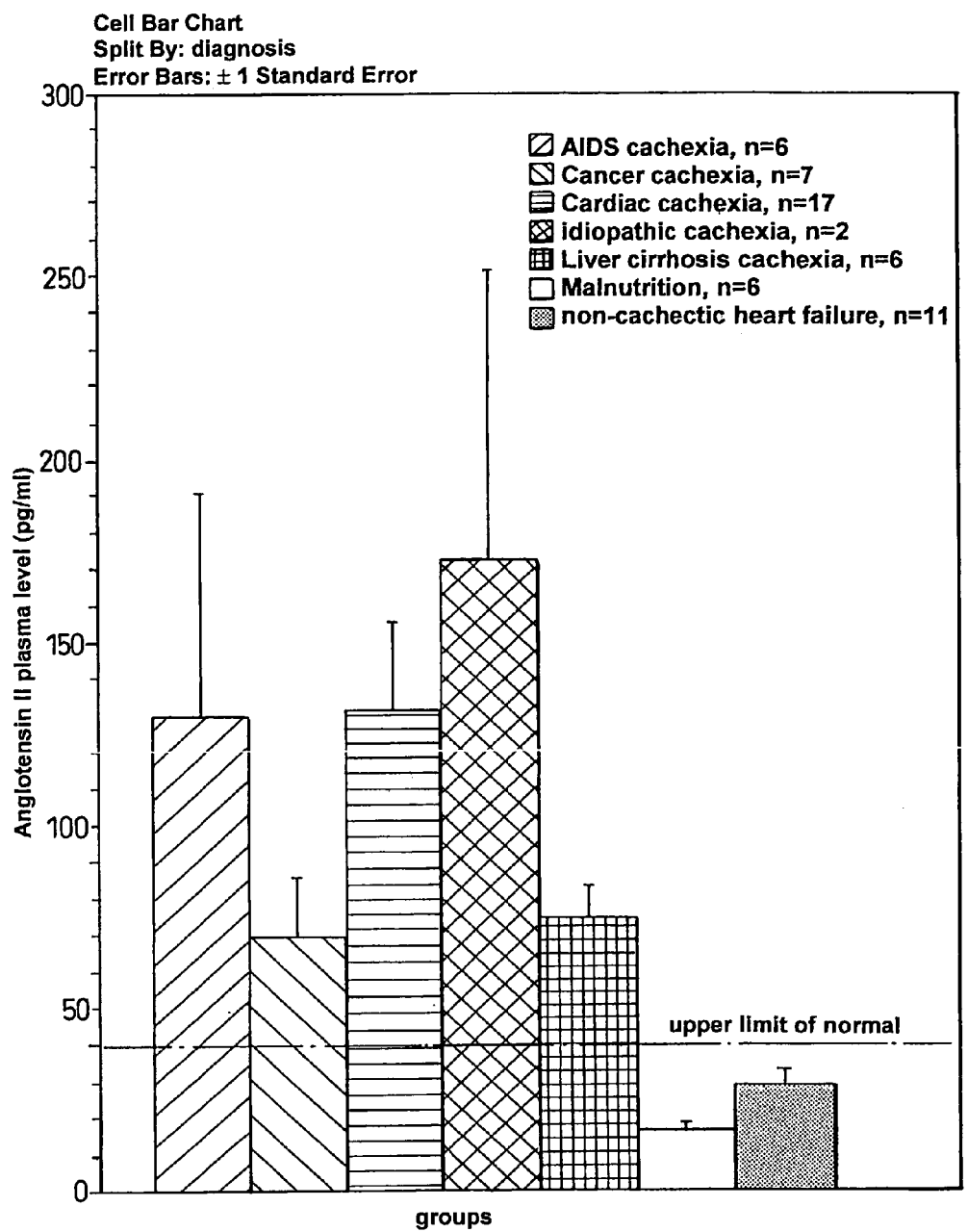
Figure 4:
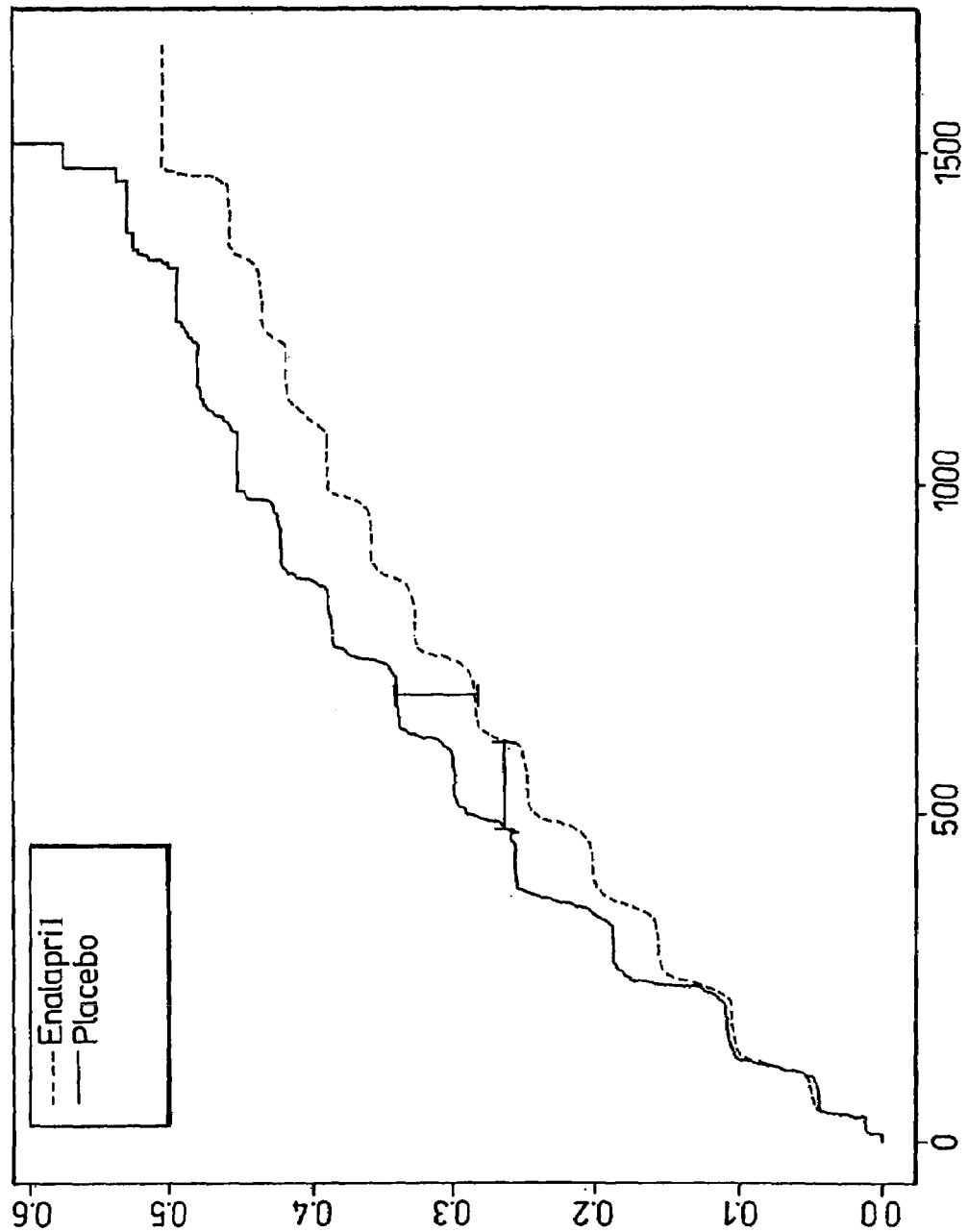
Figure 5:
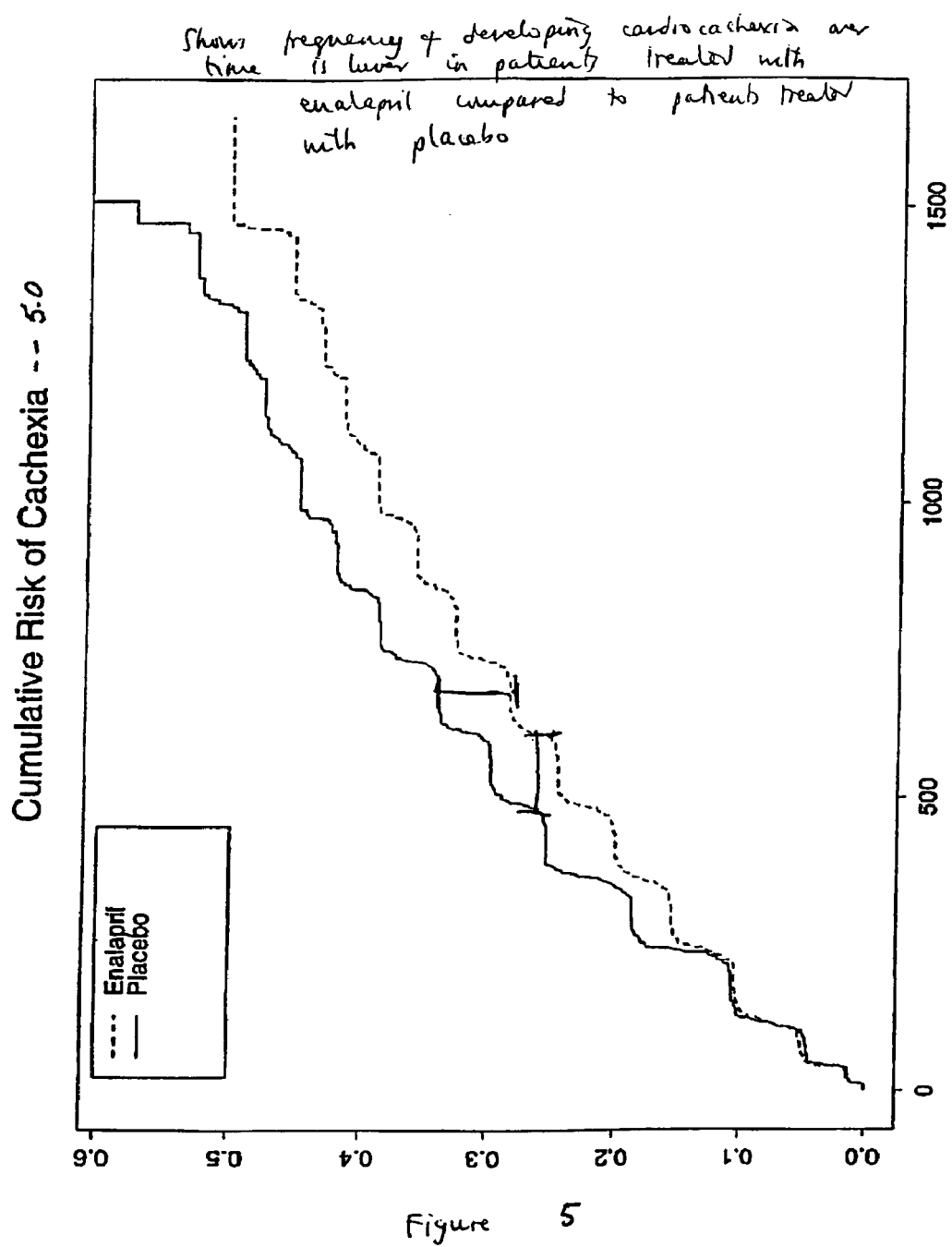

Analysis of Aldosterone Serum Levels in Cachectic Subjects with Chronic Wasting Disorders Aldosterone serum levels have been analysed hi a number of subjects with these disorders compared to healthy controls, patients with weight loss due to malnutrition (ie no active wasting disease), and CHF patients without cachexia (see Table below and FIG. 3). Patients with active wasting disease have on average 2.5 to 13-fold increased aldosterone levels compared to healthy control subjects (their mean: 43.2 ng/ml, upper limit or normal: 81 ng/ml). Patients with weight loss due to malnutrition have normal aldosterone levels. This supports our view that high aldosterone levels are pathophysiologically linked to the presence of chronic active body wasting due, ie cachexia, and that treatment with aldosterone antagonists may be beneficial.

Table: Mean Serum Aldosterone Levels in ng/ml.

Means Table for Aldosterone ng/ml

Effect: Cachexia diag.-Aldost

TABLE

Mean serum aldosterone levels in ng/ml.
Means Table for Aldosterone ng/ml
Effect: Cachexia diag.-Aldost

|  | Count | Mean | Std. Dev. | Std. Err. |
|---|---|---|---|---|
| AIDS | 4 | 105.25 | 124.14 | 62.07 |
| Cancer | 7 | 163.57 | 59.59 | 22.52 |
| cCHF | 17 | 168.18 | 102.83 | 24.94 |
| Control | 16 | 43.19 | 18.87 | 4.72 |
| Infection | 11 | 184.91 | 398.17 | 120.05 |
| Liver/cirrhosis + Cachexia | 6 | 578.17 | 297.16 | 121.32 |
| Malnutrition | 6 | 55.50 | 39.56 | 16.15 |
| ncCHF | 16 | 98.12 | 59.07 | 14.77 |
| Renal failure cachexia | 2 | 456.00 | 2.83 | 2.00 | cCHF is cachectic CHF and ncCHF is non-cachectic CHF.

We conclude that abnormalities of aldosterone-linked metabolic pathways occur in cachectic disorders independently of the specific aetiology for the cachectic disorder. Nevertheless, we find the alteration of the aldosterone pathway to be specific for cachectic disorders, as it is not seen in patients with a similar degree of weight loss consequent upon malnutrition.

Method to Measure Aldosterone:

Blood samples were collected after supine rest of at least 10 minutes. An antecubital polyethylene catheter was inserted and 10 ml of venous blood were drawn. After immediate centrifugation aliquots were stored at −70° C. until analysis. Aldosterone was measured using a commercially available competitive radioimmunoassay (DPC, Los Angeles, USA, sensitivity 10 ng/ml). This test is a coated tube assay using radio-iodinated tracer. Bound and free phases are separated by decantation. The radioactivity in the bound fractions is measured and a typical standard curve can be generated. The test has a cross-reactivity with spironolactone and aldosterone metabolites of <1% and a within test coefficient of variance is <7% and the between test variability is <10%.

EXAMPLE 3

Endothelin-1 (ET-1), TNF and Xanthine Oxidase Activity

We have previously suggested that the metabo-ergoreceptor reflex (afferents sensitive to skeletal muscle work load) [Piepoli M, Clark A L, Volterrani M, Adamopoulos S, Sleight P, Coats A J (1996) "Contribution of muscle afferents to the hemodynamic, autonomic, and ventilatory responses to exercise in patients with chronic heart failure: effects of physical training" *Circulation* 93(5), 940-952] can deliver a strong sympathetic nervous input that may finally lead to chronically raised catecholamine levels, ie that via this mechanism activation of the sympathetic nervous system (SNS) may occur. We have presented data in Example 2 that catecholamine levels are specifically raised in many cachectic syndromes.

The sensitivity of the metabo-ergoreceptor reflex response is determined by the general metabolic status of the musculature, the main determinant of the latter is the blood flow to the musculature, because via the blood flow the musculature receives its supply of oxygen and nutrients.

It is a characteristic of cachectic patients with CHF to have a poor peripheral blood flow [Anker S D, Swan J W, Volterrani M, Chua T P, Clark A L, Poole-Wilson P A, Coats A J S (1997) "The influence of muscle mass, strength, fatiguability and blood flow on exercise capacity in cachectic and non-cachectic patients with chronic heart failure" *Europ Heart J* 18, 259-269]. We have previously published that high uric acid levels [Anker S D, Leyva F, Poole-Wilson, Kox W J, Stevenson J C, A J S Coates (1997) "Relationship between serum uric acid and lower limb blood flow in patients with chronic heart failure" *Heart* 78, 39-43] and TNFα [Anker S D, Volterrani M, Egerer K R, Felton C V, Kox W J, Poole-Wilson P A, Coats A J S (1998) "Tumor necrosis factor—α as a predictor of peak leg blood flow in patients with chronic heart failure" *Q J Med* 91, 199-203] are very strong correlates of impaired peripheral blood flow in CHF patients. We now propose that treating high TNFα-levels (with TNFα-antibodies or other drugs to reduce biologically active TNF levels—like soluble TNF receptor constructs) and/or high uric acid levels (with xanthine oxidase inhibitors) may improve skeletal muscle blood flow, thereby muscle metabolic status and then metabo-ergoreceptor reflex response, and finally SNS status and the wasting disorder improve.

Another possibility to treat cachexia arises when endothelin-1 (ET-1), the strongest endogenous vasoconstrictive hormone, is considered. Its levels have never been determined in cachectic patients. We present data that ET-1 is significantly highest in cachectic CHF patients (p<0.05 vs controls and non-cachectic CHF patients, respectively), although NYHA class and left ventricular ejection fraction (LVEF) were not different between patient groups. Also age was not different between groups. CHF patients without cachexia do not show abnormal ET-1 levels.

Table: Clinical Characteristics and Endothelin-1 (ET-1) Levels in CHF Patients with and Without Cachexia and Healthy Control Subjects.

TABLE

Clinical characteristics and endothelin-1 (ET-1) levels in CHF patients with and without cachexia and healthy control subjects.

| parameter | controls n = 7 | non-cachectic CHF n = 11 | cachectic CHF n-12 |
|---|---|---|---|
| age (years) | 70 ± 2 | 66 ± 3 | 67 ± 3 |
| NYHA class | | 2.3 ± 0.1 | 2.7 ± 0.3 |
| LVEF (%) | | 34 ± 5 | 30 ± 6 |
| ET-1 (pmol/l) | 1.97 ± 0.38 | 2.22 ± 0.28 | 2.98 ± 0.20 |

Although not being bound by any theory a proposed mechanism of action is:

a) inhibition of ET-1 bioactivity by blocking ET-1 receptors, then induction of vasodilation, improvement of muscle blood flow and thereby of metabolic status, then less stimulation of SNS activation, positive effects on cachexia;

b) blocking of TNFα bioactivity, less damage to vasculature and less muscle cell damage directly (inhibition of directly detrimental effects of TNF) and indirectly (inhibition of oxygen free radical generation due to TNF action), thereby improvement of muscle blood flow and muscle cell function and thereby of muscle metabolic status, then less stimulation of SNS activation, positive effects on cachexia and wasting in general;

c) blocking of xanthine oxidase activity, less production of xanthine oxidase derived oxygen free radicals, therefore less damage to vasculature and muscle cells, thereby improvement of muscle blood flow and muscle cell function and thereby of muscle metabolic status, then less stimulation of SNS activation, positive effects on cachexia and wasting in general.

The improved muscle blood flow, muscle cell function and muscle metabolic status believed to be brought about by blocking of TNFα activity is considered to be beneficial in enhancing exercise performance in a healthy patient.

EXAMPLE 4

Cardiorespiratory Reflexes in Chronic Heart Failure (CHF) Patients with Cardiac Cachexia Cardiac cachexia in patients with chronic heart failure (CHF) predicts very poor prognosis and is linked to neurohormonal activation and an altered balance between catabolism and anabolism (in favour of catabolism).

Impaired sympatho-vagal balance in CHF is important part of neuroendocrine overactivity, is linked to a poor outcome and the underlying mechanisms remain unexplained, but overactive muscle ergoreflex system is one possible stimulus.

Having in mind the neurohormonal changes and high mortality in CHF patients with cardiac cachexia, we hypothesised that in these patients a particularly abnormal pattern of cardiorespiratory reflexes is present. The aim of the study described here was to assess whether impaired reflex control within the cardiorespiratory system (as evidenced by baroreflex inhibition, peripheral chemoreflex overactivity, and abnormal heart rate variability [HRV] patterns) is associated with the presence of cardiac cachexia rather than with conventional markers of CHF severity.

Patients

39 Stable CHF Patients Studied:
  all men, age 60 y, NYHA class: II-IV, peak $VO_2$: 17 ml/kg/min, LVEF:24%

Patients divided into 2 groups:
  13 patients with cardiac cachexia vs 26 non-cachectic CHF patients
  cachectic and noncachectic patients were matched according to age and CHF disease severity Cardiac Cachexia:
  non-intentional, non-edematous, documented weight loss >7.5% of the previous normal weight over a period of >6 months, and a BMI (=weight/height$^2$)<24 kg/m$^2$ (to exclude obese dieters)

Control Subjects
  For the comparison of the results of HRV and baroreflex sensitivity 11 healthy controls (all men, mean age: 60±7 y) were studied.
  For the comparison of the results of peripheral chemosensitivity and hormonal measurements data for healthy data for healthy control subjects from the following studies were used:
    peripheral CHEMO (chemoreflex sensitivity): Chua T P et al (1995) *Eur J Clin Invest* 25, 887
    hormonal measurements: Anker S D et al (1997) *Circulation* 96, Methods (1)

1. Evaluation of the Cardiorespiratory Reflex Control

Assessment of the Sympatho-Vagal Control of Heart Rate
  power spectral analysis of HRV derived from 20 minutes recorded the following spectral bands were identified: very low frequency (0.003-0.04 Hz, VLF), low frequency (0.05-0.14 Hz, LF), and high frequency (0.15-0.40 Hz, HF)

Peripheral Chemosensitivity Evaluation
  transient hypoxic method (the ventilatory response to hypoxia using transient inhalations of pure nitrogen)

Methods (2)

Baroreflex Sensitivity
  phenylephrine method

2. Hormonal Measurements

Fasting Venous Blood Samples
  collected in the morning (9 and 10 am)
  after patients' supine rest of at least 20 min
  levels of epinephrine and norepinephrine measured using HPLC (sensitivity 0.1 ng/mrl for both)

Results (1)

Table: HRV Measures in Controls, Non-Cachectic (ncCHF) and Cachectic (cCHF) Patients

TABLE

HRV measure in controls, non-cachectic (ncCHF) and cachectic (cCHF) patients

| | Controls | ncCHF (n = 26) | cCHF (n = 13) | p-value | |
|---|---|---|---|---|---|
| Mean RR (ms) | 1009 ± 133 | 875 ± 125 | 790 ± 181 | cCHF vs ncCHF | NS |
| | | | | cCHF vs cont | 0.0008 |
| | | | | ncCHF vs cont | 0.01 |
| TP (In ms$^2$) | 7.1 ± 0.6 | 6.7 ± 1.2 | 6.1 ± 0.7 | NS | |
| VLF (% TP) | 63 ± 12 | 76 ± 12 | 85 ± 10 | cCHF vs ncCHF | 0.07 |

TABLE-continued

HRV measure in controls, non-cachectic (ncCHF) and cachectic (cCHF) patients

|  | Controls | ncCHF (n = 26) | cCHF (n = 13) | p-value | |
|---|---|---|---|---|---|
| LF (In ms$^2$) | 5.6 ± 0.9 | 4.2 ± 1.4 | 1.7 ± 1.5 | cCHF vs cont | 0.0002 |
|  |  |  |  | ncCHF vs cont | 0.004 |
|  |  |  |  | cCHF vs ncCHF | <0.0001 |
|  |  |  |  | cCHF vs cont | <0.0001 |
|  |  |  |  | ncCHF vs cont | 0.008 |
| LF (normalised units) | 64 ± 19 | 42 ± 21 | 15 ± 18 | cCHF vs ncCHF | 0.002 |
|  |  |  |  | cCHF vs cont | <0.0001 |
|  |  |  |  | ncCHF vs cont | 0.009 |
| HF (In ms$^2$) | 4.7 ± 1.1 | 4.1 ± 1.3 | 3.3 ± 0.9 | NS | |

Results (2)

Table: Baroreflex Sensitivity, Peripheral Chemosensitivity and Hormonal Measures in Controls, Non-Cachectic (nc-CHF) and Cachectic (cCHF) Patients

TABLE

Baroflex sensitivity, peripheral chemosensitivity and hormonal measures in control, non-cachectic (ncCHF) and cachectic (cCHF) patients

|  | Controls | ncCHF (n = 26) | cCHF (n = 13) | p-value | |
|---|---|---|---|---|---|
| Baroreflex sensitivity (ms/mmHg) | 9.2 ± 4.9 | 5.5 ± 3.5 | 1.5 ± 1.9 | cCHF vs ncCHF | 0.04 |
|  |  |  |  | cCHF vs cont | 0.0005 |
|  |  |  |  | ncCHF vs cont | 0.02 |
| Peripheral chemosensitivity (L/min/% SaO$_2$) | 0.29 ± 0.21 | 0.47 ± 0.20 | 0.91 ± 0.37 | cCHF vs ncCHF | <0.0001 |
|  |  |  |  | cCHF vs cont | <0.0001 |
|  |  |  |  | ncCHF vs cont | 0.05 |
| Epinephrine (nmol/L) | 0.51 ± 0.16 | 0.68 ± 0.23 | 2.46 ± 1.74 | cCHF vs ncCHF | <0.0001 |
|  |  |  |  | cCHF vs cont | <0.0001 |
|  |  |  |  | ncCHF vs cont | NS |
| Norepinephrine (nmol/L) | 1.94 ± 0.68 | 2.34 ± 0.16 | 4.61 ± 3.92 | cCHF vs ncCHF | 0.02 |
|  |  |  |  | cCHF vs cont | <0.003 |
|  |  |  |  | ncCHF vs cont | NS |

Conclusions

1. Patients with chronic heart failure who developed cardiac cachexia demonstrate particularly abnormal reflex control within the cardiovascular and respiratory systems.
2. The nature of the link between this phenomenon and the hormonal changes and the poor prognosis of cachectic CHF patients raises the potential for novel therapeutic strategies targeting the wasting process in cachectic CHF patients by altering the reflex status of patients that could lead to less activation of the sympathetic nervous system and better symptomatic status.

EXAMPLE 5

Treatment with Atenolol

A hypertensive patient presented weighing 85.6 kg. He was treated with Losartan 50 mgs OD, Bendrofluazide 2-5 mgs OD, Doxazosin 1 mg OD and Atenolol, a β-blocker, 50 mgs OD. In 11 months his weight increased to 94.3 kg.

EXAMPLE 6

The Presence of Sympathetic Nervous System Activation and Abnormal Sympatho-Vagal Balance in AIDS-Related Wasting Disease Sympathetic nervous system (SNS) activation and abnormal sympatho-vagal balance is not only present in patients with cardiac cachexia (Example 4), but also in patients with cachexia due to other disease in the absence of heart failure or any other cardiac disease. The assessment of cardiorespiratory reflex control in 19 patients with documented AIDS disease and documented weight loss of >10% (mean 22.3±1.7%) and body mass index <20 kg/M$^2$ was compared to 9 non-cachectic AIDS patients.

The table displays the results of power spectral analyses of heart rate variability (HRV, see methods in Example 4). Statistical test: unpaired t-test. P-values are indicated.

Unpaired t-test for BMI in kg/m2

Grouping Variable: cach?AIDS

Hypothesized Difference=0

Row Exclusion: AIDS HRV-adapted 10/99-StV

|  | Mean Diff. | DF | t-Value | P-Value |
|---|---|---|---|---|
| cAIDS, ncAIDS | −5.466 | 26 | −7.349 | <.0001 |

Group Info for BMI in kg/m2

Grouping Variable: cach?AIDS

Row Exclusion: AIDS HRV-Adapted 10/99-StV

|  | Count | Mean | Variance | Std. Dev. | Std. Err |
|---|---|---|---|---|---|
| cAIDS | 19 | 17.410 | 3.438 | 1.854 | .425 |
| ncAIDS | 9 | 22.875 | 3.243 | 1.801 | .600 |

Unpaired t-test for AGE in Years

Grouping Variable: cach?AIDS

Hypothesized Difference=0

Row Exclusion: AIDS HRV-Adapted 10/99-StV

|  | Mean Diff. | DF | t-Value | P-Value |
|---|---|---|---|---|
| cAIDS, ncAIDS | −4.474 | 26 | −1.475 | .1522 |

Group Info for AGE in Years

Grouping Variable: cach?AIDS

Row Exclusion: AIDS HRV-Adapted 1 0199-StV

|  | Count | Mean | Variance | Std. Dev. | Std. Err |
|---|---|---|---|---|---|
| cAIDS | 19 | 38.526 | 58.041 | 7.618 | 1.748 |
| ncAIDS | 9 | 43.000 | 52.000 | 7.211 | 2.404 |

Unpaired t-test for ln HRV-TP (ln ms2)

Grouping Variable: cach?AIDS

Hypothesized Difference=0

Row Exclusion: AIDS HRV-Adapted 10/99-StV

|  | Mean Diff. | DF | t-Value | P-Value |
|---|---|---|---|---|
| cAIDS, ncAIDS | −.949 | 26 | −1.897 | .0690 |

Group Info for ln HRV-TP (ln ms2)

Grouping Variable: cach?AIDS

Row exclusion: AIDS HRV-Adapted 10/99-StV

|  | Count | Mean | Variance | Std. Dev. | Std. Err |
|---|---|---|---|---|---|
| cAIDS | 19 | 5.357 | 1.230 | 1.109 | .254 |
| ncAIDS | 9 | 6.306 | 2.200 | 1.483 | .494 |

From the Results Can be Concluded:

1. Cachectic AIDS patients show abnormal sympatho-vagal balance (low LF regardless of whether analysed in absolute or normalised units) compared to non-cachectic AIDS patients and healthy controls (see data in Example 4). Also overall HRV (total power: TP) was lower in cachectic vs non-cachectic AIDS patients (p<0.07). Although HF was not significantly lower in cachectic AIDS patients vs non-cachectic AIDS patients (p=0.16), it was much lower than in healthy subjects or heart failure patients (compare with data in Example 4).

2. The link between abnormal sympatho-vagal balance and hormonal/metabolic abnormalities—in cachectic AIDS patients indicates that the treatments that alter such abnormalities as described herein could have favourable effects on the wasting status of these patients and thereby exert overall beneficial effects.

EXAMPLE 7

Treatment of a Cachectic Patient with Chronic Heart Failure with an Example Beta-Blocker (Carvedilol)

We disclose herein that beta-receptor blockade is of benefit for cachectic patients—even if such patients are previously treated with an ACE inhibitor. To exemplify this, we have treated a patient with cachexia due to chronic heart failure (CHF) with an aetiology of idiopathic dilated cardiomyopathy (age 60 years, male, weight 69.2 kg, height 183 cm, previous weight loss 10.0 kg [11.6%] in 2 years, indicative of chronic weight loss) with Carvedilol (3.125 mg to 12.5 mg twice daily). We have studied body weight, clinical status, parameters of treadmill exercise capacity, and body composition at baseline and during follow-up. The patient had evidence of CHF with impaired exercise capacity and impaired left ventricular function (fractional shortening 17%) and left ventricular dilation (LVEDD 60 mm) at baseline. The patient had good compliance in taking the carvedilol.

Used Methods:

Body composition was studied using bioelectrical impedance analysis in the erect position using a body fat analyser (TANITA THF-305, Tanita Corporation, IL, USA). Lean and fat mass were automatically analysed based on equations supplied and programmed into the machine by the manufacturer. These equations are based upon a comparison with measurements in a healthy population.

Treadmill exercise testing: The patients underwent symptom limited treadmill exercise testing. A standard Bruce protocol with the addition of a "stage 0" consisting of 3 min at a speed of 1 mile per hour with a 5% gradient was used. The patients breathed through a one-way valve connected to a respiratory mass spectrometer (Amis 2000, Odense, Denmark) and minute ventilation, oxygen consumption and carbon dioxide production were calculated on line every 10 seconds using a standard inert gas dilution technique. Patients were encouraged to exercise to exhaustion. Exercise time and oxygen consumption at peak exercise adjusted for total body weight (peak VO, in nil/kg/min) were measured as an index of the exercise capacity.

Result:

The results show that the patient had an improvement in exercise capacity (peak $VO_2$ increase of 15%) and in respiratory efficiency indicated by an improvement in $VE/VCO_2$-slope, which decreased by 15.5%. The increase in exercise capacity was associated with an increase in lean muscle tissue (increased by 1.8 kg). The improvement in $VE/VCO_2$-slope indicates that muscle metabolic status and reflex status may have additionally improved. In this patient body weight increased by 2.1 kg (3.1%), without development of oedema. The patient tolerated the treatment well.

Conclusion:

Beta-blocker treatment was shown to be beneficial in a cachectic patient.

EXAMPLE 8

Treatment of Cachexia Patients with an Aldosterone Antagonist (Spironolactone)

We disclose herein that the blockade of the aldosterone pathway is of benefit for cachectic patients—even if such patients are previously treated with an ACE inhibitor. To exemplify this, we have treated a patient with cachexia due to chronic heart failure (CHF) on the background of coronary artery disease (age 76 years, male, weight 76.0 kg, height 182 cm, previous weight loss 10.0 kg [11.6%] in 3 years, indicative of chronic weight loss) with spironolactone (25 mg once daily). We have studied body weight, clinical status and parameters of treadmill exercise capacity at baseline and during follow-up. The patient had evidence of CHF with impaired exercise capacity and impaired left ventricular ejection fraction (LVEF 34%) and left ventricular end-diastolic dimension (LVEDD 72 mm) at baseline. The patient had good compliance in taking spironolactone.

Used Methods:

Treadmill exercise testing: The patient underwent symptom limited treadmill exercise testing. A standard Bruce protocol was used. The patient breathed through a one-way valve connected to a commercially available respiratory gas analyser (MedGraphics Inc., USA) and minute ventilation and oxygen consumption were recorded on line every 15 seconds. The patient was encouraged to exercise to exhaustion. Exercise time and oxygen consumption at peak exercise adjusted for total body weight (peak $VO_2$ in ml/kg/min) was measured as an index of the exercise capacity. One day prior to the intended baseline exercise test an additional exercise test was performed to familarise the patient with the test procedure.

Results:

The results show that the patient had a dramatic improvement in exercise capacity (peak $VO_2$ increase of 79%, exercise time increased by 53%), the symptomatic New York Heart Association functional class (NYHA class) improved from class III symptoms to class II symptoms. We have evidence that in this patient body weight increased by 1.5 kg (2%), without development of any oedema. We observed no side effects of the treatment. The improvement of exercise capacity and increase in oxygen consumption was achieved on the basis of a stable peak ventilation, ie it can be concluded that also ventilatory efficiency increased.

Conclusion:

It is well known that the peak oxygen consumption of CHF patients most significantly correlates with leg muscle (lean) tissue mass (Anker et al (1998) *Am J. Cardiol.* 83, 612-615). The strong increase in peak oxygen consumption is indicative of the weight increase mainly reflecting an increase of leg muscle tissue. Additionally, the increase in ventilatory efficiency indicates improved ventilatory reflex status which, we think, is due to improved muscle metabolic status. Aldosterone antagonist treatment was shown to be beneficial in a cachectic patient.

The invention claimed is:

1. A method of treating cachexia in a patient, the method comprising administering to the patient an agent selected from the group consisting of a β receptor blocker or a compound which inhibits the effect of aldosterone in an effective amount to reduce sympathetic nervous system activity.

2. The method according to claim 1 wherein the compound which inhibits the effect of aldosterone is an aldosterone antagonist.

3. The method according to claim 2 wherein the aldosterone antagonist is selected from the group consisting of spironolactone, testolactone, RU40555, RU26752, canrenoate, eplerenone, 3-(17β-hydroxy-3-oxoandrosta-1,4,6,11-tetraen-17α-yl) propionic acid γ lactone, 3-(9-α-fluoro-17β-hydroxy-3-oxo-androsta-4-en-17α-yl) propionic acid γ lactone, dihydro-spirorenone, spirorenone, 15,16-methylene derivatives of spironolactone, mespirenone and SC9420.

4. The method according to claim 1 wherein the β receptor blocker is selected from the group consisting of acebutolol, alprenolol, atenolol, betaxolol, bisoprolol, carteolol, celiprolol, esmolol, labetolol, lavobunolol, metipranolol, metoprolol, nadolol, oxprenolol, penbutolol, pindolol, propanolol, sotalol, timolol, nebivolol, carvedilol and bucindolol.

5. The method of claim 1 wherein the drug reduces sympathetic nervous system activity by affecting cardiovascular reflexes.

6. The method according to claim 1 wherein the cachexia results from an underlying disease is selected from the group consisting of AIDS, liver cirrhosis, chronic obstructive pulmonary disease with or without emphysema, chronic renal failure, chronic infections, cancer, heart disease including hypertension and chronic heart failure.

7. The method according to claim 1 wherein the patient has idiopathic cachexia.

8. The method according to claim 1 wherein the underlying disease is chronic heart failure and the patient has cardiac cachexia.

9. The method of claim 1 wherein the β receptor blocker is bucindolol.

10. The method of claim 1 wherein the β preceptor blocker is nebivolol.

* * * * *

UNITED STATES PATENT AND TRADEMARK OFFICE
CERTIFICATE OF CORRECTION

PATENT NO. : 7,417,038 B1  Page 1 of 1
APPLICATION NO. : 09/807558
DATED : August 26, 2008
INVENTOR(S) : Stefan Dietmar Anker and Andrew Justin Stewart Coats It is certified that error appears in the above-identified patent and that said Letters Patent is hereby corrected as shown below:

Claim 6, column 24, line 28, delete "is".

Signed and Sealed this

Seventeenth Day of February, 2009

JOHN DOLL
*Acting Director of the United States Patent and Trademark Office*